United States Patent
Murray et al.

(10) Patent No.: US 10,041,067 B2
(45) Date of Patent: Aug. 7, 2018

(54) METHODS AND COMPOSITIONS FOR RAPID ASSEMBLY OF GENETIC MODULES

(71) Applicant: California Institute of Technology, Pasadena, CA (US)

(72) Inventors: Richard Martin Murray, Pasadena, CA (US); Zachary Z. Sun, San Francisco, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/140,105

(22) Filed: Apr. 27, 2016

(65) Prior Publication Data

US 2016/0312215 A1 Oct. 27, 2016

Related U.S. Application Data

(60) Provisional application No. 62/153,308, filed on Apr. 27, 2015.

(51) Int. Cl.
*C12N 15/10* (2006.01)
*C12N 15/66* (2006.01)

(52) U.S. Cl.
CPC ......... *C12N 15/1093* (2013.01); *C12N 15/66* (2013.01)

(58) Field of Classification Search
None
See application file for complete search history.

(56) References Cited

U.S. PATENT DOCUMENTS

2002/0025561 A1 2/2002 Hodgson

FOREIGN PATENT DOCUMENTS

WO 2011/154147 12/2011
WO 2014/071182 5/2014

OTHER PUBLICATIONS

Adreadis et al., Nuc. Acids Res. 28 (2) : e5 , 2000.*
Sarrion-Perdigones, Alejandro et al., "GoldenBraid: an interactive cloning system for standardization assembly of reusable genetic modules", PLOS ONE, vol. 6, No. 7, e21622, Jul. 7, 2011.
Werner, Stefan et al., "Fast track assembly of multigene constructs using Golden Gate cloning and the MoClo system", Bioengineered Bugs, vol. 3, No. 1, pp. 38-43, Jan. 1, 2012.
PCT International Search Report and Written Opinion issued in International Application No. PCT/US2016/029565 dated Aug. 9, 2016.
Engler, C., et al., "Golden Gate Shuffling: A One-Pot DNA Shuffling Method Based on Type IIs Restriction Enzymes", PLoS ONE, vol. 4, Issue 5, May 2009.
Sun, Z. et al., "Linear DNA for Rapid Prototyping of Synthetic Biological Circuits in *Escherichia coli* Based TX-TL Cell-Free System", ACS Synth Biol. Jun. 20, 2014;3(6):387-97.

* cited by examiner

*Primary Examiner* — Nancy A Treptow
(74) *Attorney, Agent, or Firm* — Greenberg Traurig, LLP; Fang Xie

(57) ABSTRACT

Provided herein are methods and compositions for rapid assembly of genetic modules, as well as seamless transition from in vitro to in vivo testing of genetic constructs.

20 Claims, 20 Drawing Sheets

SEQUENCE LISTING

<160> NUMBER OF SEQ ID NOS: 15

<210> SEQ ID NO 1
<211> LENGTH: 28
<212> TYPE: DNA
<213> ORGANISM: Unknown
<220> FEATURE:
<223> OTHER INFORMATION: Synthetic

<400> SEQUENCE: 1
gaagacaacc acgcatagag accaggac                                           28

<210> SEQ ID NO 2
<211> LENGTH: 28
<212> TYPE: DNA
<213> ORGANISM: unknown
<220> FEATURE:
<223> OTHER INFORMATION: synthetic

<400> SEQUENCE: 2
gaagacaaca tagcatagag acccacct                                           28

-continued

```
<210> SEQ ID NO 3
<211> LENGTH: 16
<212> TYPE: DNA
<213> ORGANISM: unknown
<220> FEATURE:
<223> OTHER INFORMATION: synthetic

<400> SEQUENCE: 3
agaacggtct cagcat                                                      16

<210> SEQ ID NO 4
<211> LENGTH: 16
<212> TYPE: DNA
<213> ORGANISM: unknown
<220> FEATURE:
<223> OTHER INFORMATION: synthetic

<400> SEQUENCE: 4
aagctgagac cttacg                                                      16

<210> SEQ ID NO 5
<211> LENGTH: 16
<212> TYPE: DNA
<213> ORGANISM: unknown
<220> FEATURE:
<223> OTHER INFORMATION: synthetic

<400> SEQUENCE: 5
agccaggtct caaagc                                                      16

<210> SEQ ID NO 6
<211> LENGTH: 16
<212> TYPE: DNA
<213> ORGANISM: unknown
<220> FEATURE:
<223> OTHER INFORMATION: synthetic

<400> SEQUENCE: 6
aatgtgagac cgggga                                                      16

<210> SEQ ID NO 7
<211> LENGTH: 16
<212> TYPE: DNA
<213> ORGANISM: unknown
<220> FEATURE:
<223> OTHER INFORMATION: synthetic

<400> SEQUENCE: 7
aacagggtct caaatg                                                      16

<210> SEQ ID NO 8
<211> LENGTH: 16
<212> TYPE: DNA
<213> ORGANISM: unknown
<220> FEATURE:
<223> OTHER INFORMATION: synthetic

<400> SEQUENCE: 8
tgaatgagac cactaa                                                      16

<210> SEQ ID NO 9
<211> LENGTH: 16
<212> TYPE: DNA
<213> ORGANISM: unknown
<220> FEATURE:
<223> OTHER INFORMATION: synthetic
```

```
<400> SEQUENCE: 9
ggctcggtct catgaa                                                    16

<210> SEQ ID NO 10
<211> LENGTH: 16
<212> TYPE: DNA
<213> ORGANISM: unknown
<220> FEATURE:
<223> OTHER INFORMATION: synthetic

<400> SEQUENCE: 10
gtcgtgagac ccggac                                                    16

<210> SEQ ID NO 11
<211> LENGTH: 28
<212> TYPE: DNA
<213> ORGANISM: unknown
<220> FEATURE:
<223> OTHER INFORMATION: synthetic

<400> SEQUENCE: 11
atataggtct ctgtcgggca ttgtcttc                                       28

<210> SEQ ID NO 12
<211> LENGTH: 28
<212> TYPE: DNA
<213> ORGANISM: unknown
<220> FEATURE:
<223> OTHER INFORMATION: synthetic

<400> SEQUENCE: 12
tagcgggtct ctgtcgtgcc ttgtcttc                                       28

<210> SEQ ID NO 13
<211> LENGTH: 16
<212> TYPE: DNA
<213> ORGANISM: unknown
<220> FEATURE:
<223> OTHER INFORMATION: synthetic

<400> SEQUENCE: 13
gaagacaacc acgcat                                                    16

<210> SEQ ID NO 14
<211> LENGTH: 23
<212> TYPE: DNA
<213> ORGANISM: unknown
<220> FEATURE:
<223> OTHER INFORMATION: synthetic

<400> SEQUENCE: 14
ttctcatgtt tgacagctta tca                                            23

<210> SEQ ID NO 15
<211> LENGTH: 21
<212> TYPE: DNA
<213> ORGANISM: unknown
<220> FEATURE:
<223> OTHER INFORMATION: synthetic

<400> SEQUENCE: 15
ataactcaaa aaatacgccc g                                              21
```

METHODS AND COMPOSITIONS FOR RAPID ASSEMBLY OF GENETIC MODULES

CROSS REFERENCE TO RELATED APPLICATIONS

This application claims priority to and the benefit of U.S. Provisional Application No. 62/153,308 filed Apr. 27, 2015, the disclosure of which is hereby incorporated by reference in its entirety.

STATEMENT REGARDING GOVERNMENT LICENSE RIGHTS

This invention was made with government support under contract number HR0011-12-C-0065 awarded by the U.S. Defense Advanced Research Projects Agency (DARPA) Living Foundries Program. The government has certain rights in the invention.

FIELD

The disclosure relates to methods and compositions for rapid in vitro assembly of genetic modules, in particular pre-made DNA modules. The assembly technique disclosed herein enables seamless transition from in vitro to in vivo testing of genetic constructs.

BACKGROUND

Synthetic biology has emerged as a useful approach to decoding fundamental laws underlying biological control. Recent efforts have produced many systems and approaches and generated substantial insights on how to engineer biological functions and efficiently optimize synthetic pathways.

Despite efforts and progresses, current approaches to perform such engineering are often laborious, costly and difficult. Challenges still remain in developing engineering-driven approaches and systems to accelerate the design-build-test cycles required for reprogramming existing biological systems, constructing new biological systems and testing genetic circuits for transformative future applications in diverse areas including biology, engineering, green chemistry, agriculture and medicine.

An in vitro transcription-translation (TX-TL) system (Shin & Noireaux, 2012; Sun et al., 2013) has been developed which allows for the rapid prototyping of genetic constructs (Sun, et al., 2014) in an environment that behaves similarly to a cell (Niederholtmeyer et al., 2015; Takahashi et al., 2015). One of the main purposes of working in vitro is to be able to learn or characterize a circuit for future implementation in vivo (Chappell et al., 2013; Niederholtmeyer et al., 2015). However, there are no easy ways to convert deoxyribonucleic acid (DNA), which was created primarily for in vitro testing, to make the DNA compatible for the in vivo environment when implemented on plasmid. In specific, origins of replication need to be in compatible families, and antibiotic resistance markers need to be varied per plasmid. Thus, a need exists for new techniques that can overcome these challenges.

SUMMARY

Provided herein are methods and compositions for rapid assembly of genetic modules, as well as seamless transition from in vitro to in vivo testing of genetic constructs.

In one aspect, a method for in vitro assembly of genetic modules is provided, comprising:
a) providing recombinant transcription units Tu1, Tu2 and TuN wherein N>=3, each recombinant transcription unit being present in a separate stage 1 vector and flanked by a first pair of restriction sites of a first type IIs enzyme, wherein the first pair of restriction sites for each recombinant transcription unit are pre-designed such that upon digestion by the first type IIs enzyme, compatible cohesive ends are generated to allow ligation of the recombinant transcription units in a predetermined order 5'-Tu1-TuN-Tu2-3';
b) providing a stage 2 vector having a second pair of restriction sites of the first type IIs enzyme, wherein the second pair of restriction sites are pre-designed such that upon digestion by the first type IIs enzyme, a first and second cohesive end are generated to allow ligation of the first cohesive end with Tu1 at its 5' end and ligation of the second cohesive end with Tu2 at its 3' end; and
c) assembling the recombinant transcription units and the stage 2 vector into a plasmid in a one-pot reaction comprising the first type IIs enzyme and a ligase.

Another aspect relates to a method for in vitro assembly of genetic modules, comprising:
a) providing recombinant transcription units Tu1 and Tu2, each recombinant transcription unit being present in a separate stage 1 vector and flanked by a first pair of restriction sites of a first type IIs enzyme, wherein the first pair of restriction sites for each recombinant transcription unit are pre-designed such that upon digestion by the first type IIs enzyme, compatible cohesive ends are generated to allow ligation of the recombinant transcription units in a predetermined order 5'-Tu1-Tu2-3';
b) providing a stage 2 vector having a second pair of restriction sites of the first type IIs enzyme, wherein the second pair of restriction sites are pre-designed such that upon digestion by the first type IIs enzyme, a first and second cohesive end are generated to allow ligation of the first cohesive end with Tu1 at its 5' end and ligation of the second cohesive end with Tu2 at its 3' end;
c) assembling the recombinant transcription units and the stage 2 vector into a plasmid in a one-pot reaction comprising the first type IIs enzyme and a ligase; and
d) amplifying the recombinant transcription units in a polymerase chain reaction, using a first and second primer that span the first and second cohesive end, respectively, wherein the first primer partially anneals with the stage 2 vector at Tm<40° C. and partially with Tu1 at Tm<40° C., and the second primer partially anneals with the stage 2 vector at Tm<40° C. and partially with Tu2 at Tm<40° C.

A further aspect relates to a method for in vitro assembly of genetic modules, comprising:
a) providing recombinant transcription units Tu1, Tu2 and TuN wherein N>=3, each recombinant transcription unit being present in a separate stage 1 vector and flanked by a first pair of restriction sites of a first type IIs enzyme, wherein the first pair of restriction sites for each recombinant transcription unit are pre-designed such that upon digestion by the first type IIs enzyme, compatible cohesive ends are generated to allow ligation of the recombinant transcription units in a predetermined order 5'-Tu1-TuN-Tu2-3';

b) providing a stage 2 vector having a second pair of restriction sites of the first type IIs enzyme, wherein the second pair of restriction sites are pre-designed such that upon digestion by the first type IIs enzyme, a first and second cohesive end are generated to allow ligation of the first cohesive end with Tu1 at its 5' end and ligation of the second cohesive end with Tu2 at its 3' end;

c) assembling the recombinant transcription units and the stage 2 vector into a plasmid in a one-pot reaction comprising the first type IIs enzyme and a ligase; and d) subjecting the plasmid to expression selected from:
  in vitro expression in an in vitro transcription-translation system, and/or
  in vivo expression following transformation into a host cell.

In some embodiments in connection with any methods for in vitro assembly disclosed herein, N can be an integer between, and inclusive of, 3 and 9, i.e., 3, 4, 5, 6, 7, 8, or 9. For example, N can be 3, 4, 5 or 6.

In various embodiments, the first type IIs enzyme may be selected from BasI, Eco31I, BspTN1, Bso31I, BbsI, BpuAI, BpiI, BstV21, BsmBI, Esp3I, FokI, AlwI, and BfiII. In some embodiments, the directionality of the first pair of restriction sites can be in tandem or opposing (converging or diverging). In one example, the first pair of restriction sites can be designed to oppose each other in a converging direction.

The method can, in some embodiments, further include constructing each recombinant transcription unit from a promoter, an untranslated region, a coding sequence and a terminator, wherein one or more of the promoter, untranslated region, coding sequence and terminator are provided from a library of modular components. Each modular component can be designed and engineered to have flanking restriction sites of a second type IIs enzyme. The second type IIs enzyme can be selected from BsaI, Eco31I, BspTN1, Bso31I, BbsI, BpuAI, BpiI, BstV21, BsmBI, Esp3I, FokI, AlwI, and BfiII. The method may further include selecting the one or more of the promoter, untranslated region, coding sequence and terminator from the library.

In certain embodiments, each stage 1 vector may include a different origin of replication and/or a different selectable marker. Two or more of the stage 1 vectors may have the same origin of replication and/or the same selectable marker. Any origins of replication commonly used in molecular cloning may be used, such as colE1, pSC101, p15A, pBBR1, pMB1 and R6K. The selectable marker can be any marker commonly used in molecular cloning, such as AmpR, KanR, CmR, ZeoR, TetR, SpecR, StrepR, NeoR, and BleR.

The directionality of the second pair of restriction sites in the stage 2 vector can be in tandem or opposing (converging or diverging). In one example, the second pair of restriction sites can be designed to oppose each other in a diverging direction. In some embodiments, the stage 2 vector can include an additional pair of restriction sites of a second type IIs enzyme that flank the second pair of restriction sites of the first type IIs enzyme. The second type IIs enzyme can be selected from BsaI, Eco31I, BspTN1, Bso31I, BbsI, BpuAI, BpiI, BstV21, BsmBI, Esp3I, FokI, AlwI, and BfiII.

The method can further include a step of cycling the recombinant transcription units between the stage 1 and stage 2 vectors to produce 2 or more copies of the recombinant transcription units.

The method can, in some embodiments, further include providing two or more stage 2 vectors in step (b), and assembling in step (c) the recombinant transcription units and the two or more stage 2 vectors into two or more plasmids. Each stage 2 vector may have the same or different origin of replication and/or selectable marker. In some embodiments, up to three plasmids can be assembled in step (c) for, e.g., transformation.

In various embodiments, the plasmid assembled can be subjected to expression. The plasmid may be subjected to expression in an in vitro transcription-translation system. The plasmid may also be subjected to in vivo expression following transformation into a host cell. To facilitate in vitro expression, it may be desirable to amplify the recombinant transcription units in a polymerase chain reaction (PCR) prior to expression. In some embodiments, specific PCR primers can be designed, such as a first and second primer that span the first and second cohesive end, respectively, wherein the first primer partially anneals with the stage 2 vector at Tm<40° C. and partially with Tu1 at Tm<40° C., and the second primer partially anneals with the stage 2 vector at Tm<40° C. and partially with Tu2 at Tm<40° C. In some embodiments, the total Tm for each primer is designed to be about 55-65° C., about 58-62° C. or about 60° C.

Also provided herein is a non-naturally occurring library of genetic modules, comprising:
  a plurality of pre-designed promoters,
  a plurality of pre-designed untranslated regions,
  a plurality of pre-designed terminators,
  a plurality of pre-designed stage 1 vectors, and
  at least one pre-designed stage 2 vector,
  wherein each promoter, untranslated region, terminator, stage 1 vector and stage 2 vector are engineered to have a pair of restriction sites of a first type IIs enzyme.

In some embodiments, the stage 1 and stage 2 vectors can each further comprise a pair of restriction sites of a second type IIs enzyme. The first and/or second type IIs enzyme can be selected from BsaI, Eco31I, BspTN1, Bso31I, BbsI, BpuAI, BpiI, BstV21, BsmBI, Esp3I, FokI, AlwI, and BfiII. The first and second type IIs enzymes are different in certain embodiments.

A further aspect relates to a kit for in vitro assembly of genetic modules, comprising:
  a) any library of genetic modules disclosed herein, and
  b) instruction for in vitro assembly of a coding sequence of interest with a promoter, an untranslated region and a terminator selected from the library into a transcription unit in a stage 1 vector, and further assembly of a plurality of transcription units into a stage 2 vector.

The method, library and kit disclosed herein can be used for rapid assembly of any genetic circuit of interest, or one or more portions thereof. The assembled genetic circuit or portion thereof is compatible with the in vivo environment and thus, can be seamlessly transitioned from in vitro to in vivo testing.

BRIEF DESCRIPTION OF THE FIGURES

The presently disclosed technology will be further explained with reference to the attached drawings. The drawings shown are not necessarily to scale, with emphasis instead generally being placed upon illustrating the principles of the presently disclosed technology.

FIG. 8A illustrates an assembly map of 5 stage 1 constructs into 1 stage 2 construct. FIG. 8B illustrates the testing of the stage 1 linear DNA constructs in vitro in a cell-free transcription-translation system. FIG. 8C illustrates the testing of the stage 2 construct in vivo.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Compositions and methods disclosed herein relate to methods, libraries and kits for rapid in vitro assembly of any genetic circuit of interest, or one or more portions (subcircuits) thereof. The assembled genetic circuit or portion thereof is, by design, compatible with the in vivo environment. The technology disclosed herein therefore permits the seamlessly transition from in vitro to in vivo testing. Significantly, the rapid, entirely in vitro assembly technique disclosed herein can be used to assemble regulatory elements and basic circuits from standard or custom pieces in, e.g., under 4 h, with complete testing in, e.g., under 8 h. By maintaining an engineering cycle time of 8 h or less, the present technology enables prototyping of multicomponent circuits in a standard business day or less.

Figure 1:
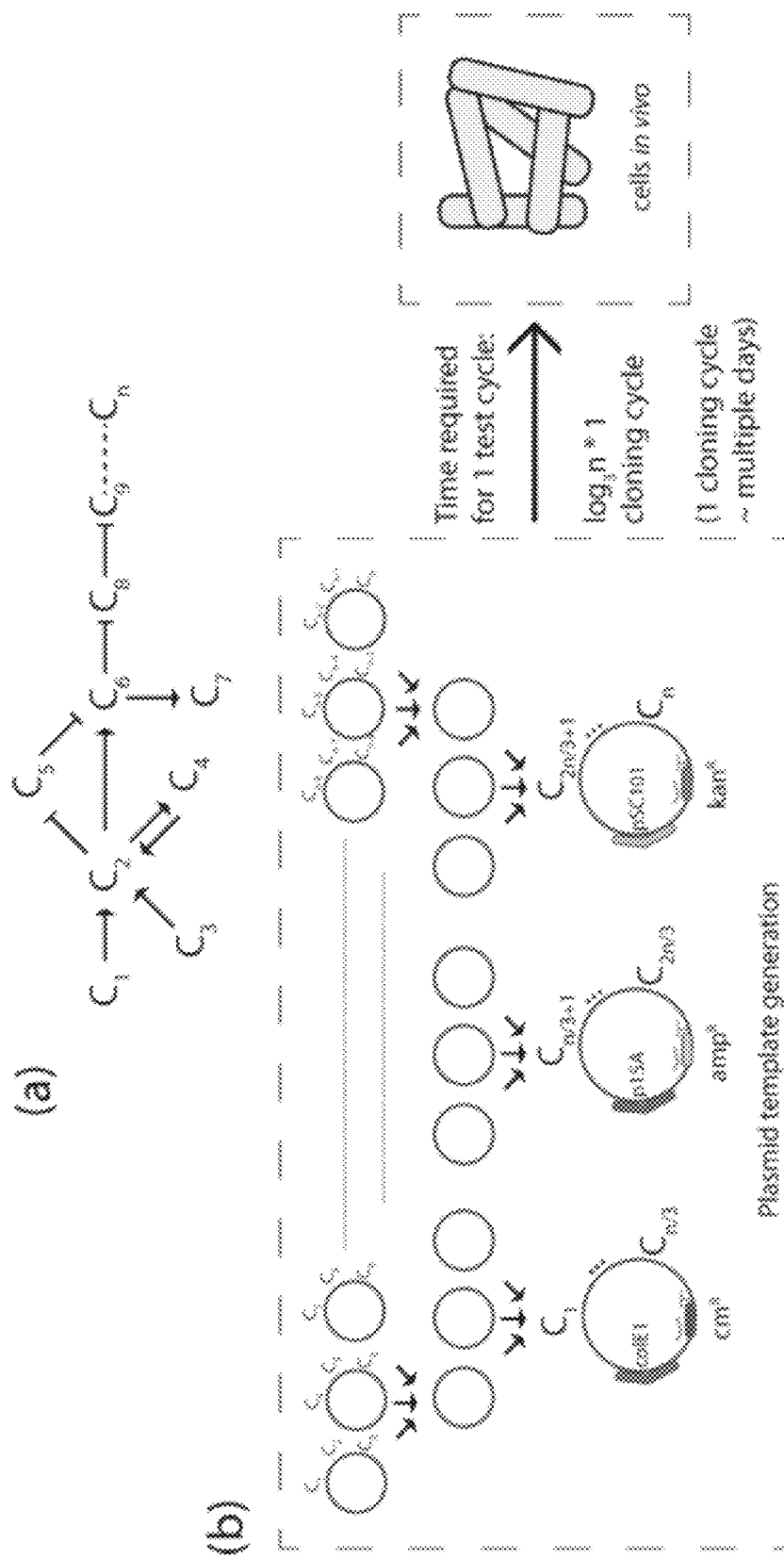
FIG. 1 illustrates, in panel (a), a hypothetical circuit composed of n components to be prototyped in vivo or in TX-TL, and in panel (b), conventional prototyping in vivo that requires the reduction of n components to 3 plasmids, which can then be transformed into a cell.

In contrast, conventional technology requires step-by-step cloning and testing of each part of a multicomponent circuit, before the complete circuit can be cloned into a plasmid for propagation in vivo. This is a labor-intensive and serial process that has a 1-week testing cycle, which scales poorly for complex circuits (FIG. 1, panel a). Although large-scale successes have been accomplished by this testing method, there is a significant time cost to this engineering cycle. For example, the industrial production of artemisinin from synthetic circuits in *E. coli* and *S. cerevisiae* has taken 150 "person-years," of which much time can be attributed to part testing. As further illustrated in FIG. 1, panels (a) and (b), to initially test an n-part circuit in vivo would require $\log_3(n)$ rounds of plasmid cloning, assuming assemblies of 5 pieces at the same time (four regulatory units plus a vector backbone). This restriction results from the carrying capacity of the cell of a maximum of 3 different plasmids to maintain a limited number of antibiotic cassettes and origins of replication.

Using the rapid in vitro assembly approach disclosed herein, the present disclosure circumvents the conventional molecular cloning process that is costly and labor intensive. Engineering-driven approaches and systems are provided herein that significantly accelerate the design-build-test cycles required for reprogramming existing biological systems, constructing new biological systems and testing genetic circuits useful in many areas including biology, engineering, green chemistry, agriculture and medicine.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

The articles "a" and "an" are used herein to refer to one or to more than one (i.e., at least one) of the grammatical object of the article. By way of example, "an element" means one element or more than one element.

As used herein, the term "about" means within 20%, more preferably within 10% and most preferably within 5%. The term "substantially" means more than 50%, preferably more than 80%, and most preferably more than 90% or 95%.

As used herein, "a plurality of" means more than 1, e.g., 2, 3, 4, 5, 6, 7, 8, 9, 10, 11, 12, 13, 14, 15, 16, 17, 18, 19, 20, or more, e.g., 25, 30, 40, 50, 60, 70, 80, 90, 100, 200, 300, 400, 500, or more, or any integer therebetween.

As used herein, the terms "nucleic acid," "nucleic acid molecule" and "polynucleotide" may be used interchangeably and include both single-stranded (ss) and double-stranded (ds) RNA, DNA and RNA:DNA hybrids. These terms are intended to include, but are not limited to, a polymeric form of nucleotides that may have various lengths, including deoxyribonucleotides and/or ribonucleotides, or analogs or modifications thereof. A nucleic acid molecule may encode a full-length polypeptide or RNA or a fragment of any length thereof, or may be non-coding.

Nucleic acids can be naturally-occurring or synthetic polymeric forms of nucleotides. The nucleic acid molecules of the present disclosure may be formed from naturally-occurring nucleotides, for example forming deoxyribonucleic acid (DNA) or ribonucleic acid (RNA) molecules. Alternatively, the naturally-occurring oligonucleotides may include structural modifications to alter their properties, such as in peptide nucleic acids (PNA) or in locked nucleic acids (LNA). The terms should be understood to include equivalents, analogs of either RNA or DNA made from nucleotide analogs and as applicable to the embodiment being described, single-stranded or double-stranded polynucleotides. Nucleotides useful in the disclosure include, for example, naturally-occurring nucleotides (for example, ribonucleotides or deoxyribonucleotides), or natural or synthetic modifications of nucleotides, or artificial bases. Modifications can also include phosphorothioated bases for increased stability.

"Assembly" or "assemble" means a process in which nucleic acid fragments (e.g., genetic modules as defined hereunder) are operably linked with one another in a pre-designed order to form a longer nucleic acid sequence. For example, genetic modules (also referred to as "stage 0 pieces" or "pieces" in the context of assembly in some embodiments) can be assembled into transcription units or parts. The transcription units can be present in linear format or in a circular plasmid, which is sometimes referred to as "stage 1 constructs." Two or more transcription units can be assembled into a complete or partial circuit, sometimes referred to as "stage 2 constructs." In some embodiments, assembly can be achieved using pre-selected cohesive ends that define the pre-designed order of genetic modules or transcription units in the assembled product. A first nucleic acid sequence is "operably linked" with a second nucleic acid sequence when the sequences are so arranged that the first nucleic acid sequence affects the function of the second nucleic acid sequence. Preferably, the two sequences are part of a single contiguous nucleic acid molecule and more preferably are adjacent. For example, a promoter is operably linked to a gene or a coding sequence if the promoter regulates or mediates transcription of the gene in a cell.

A "circuit" or "genetic circuit" as used herein refers to a collection of parts (also referred to as "transcription units" or "Tu" in some embodiments) that undergo transcription and/or translation to produce mRNA or proteins, respectively (each an "output" of the part). The part output can interact with other parts (for example to regulate transcription or translation) or can interact with other molecules in the cell (e.g., small molecules, DNA, RNA or proteins that are present in the cellular environment). For example, a circuit can be a metabolic pathway or a genetic cascade, which can be naturally occurring or non-naturally occurring, artificially engineered. Each part in the circuit can include a set of components or genetic modules, e.g., a promoter, ribosome binding site (RBS), coding sequence (CDS) and/or terminator. These components may be interconnected or assembled in different ways to implement different parts, and the resultant parts may be combined in different ways to create different circuits or pathways. In addition to these parts, the circuit may contain additional molecular species that are present in a cell or in the cell's environment that the components interact with.

As described herein, "genetic module" and "genetic element" may be used interchangeably and refer to any coding and/or non-coding nucleic acid sequence. Genetic modules may be operons, genes, gene fragments, promoters, exons, introns, regulatory sequences, or any combination thereof. In some embodiments, a genetic module refers to one or more of coding sequence, promoter, terminator, untranslated region, ribosome binding site, polyadenylation tail, leader, signal sequence, vector and any combination of the foregoing. In certain embodiments, a genetic module can be a transcription unit as defined herein.

Genetic modules may be derived from the genome of natural organisms or from synthetic polynucleotides or a combination thereof. In some embodiments, the genetic modules are derived from different organisms. Genetic modules useful for the methods described herein may be obtained from a variety of sources such as, for example, DNA libraries, BAC (bacterial artificial chromosome) libraries, de novo chemical synthesis, commercial gene synthesis or excision and modification of a genomic segment. The sequences obtained from such sources may then be modified using standard molecular biology and/or recombinant DNA technology. Exemplary methods for modification of polynucleotide sequences include, for example, site directed mutagenesis; PCR mutagenesis; inserting, deleting or swapping portions of a sequence using restriction enzymes optionally in combination with ligation; in vitro or in vivo homologous recombination; and site-specific recombination; or various combinations thereof. In other embodiments, the genetic sequences useful in accordance with the methods described herein may be synthetic oligonucleotides or polynucleotides produced by any methods known in the art.

In some embodiments, genetic modules share less than 99%, less than 95%, less than 90%, less than 80%, or less than 70% sequence identity with a native or natural nucleic acid sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for alignment are described by Doolittle, Methods Enzymol. 1996; 266:368-82. Preferably, an alignment program that permits gaps in the sequence is utilized to align the sequences. The Smith-Waterman is one type of algorithm that permits gaps in sequence alignments. Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer.

A "library" of genetic modules refers to a collection of pre-made, standard genetic modules. The library can be pre-designed such that each module therein has been engineered to generate compatible cohesive ends upon, e.g., restriction enzyme digestion. In one example, all genetic modules within a library can be designed to be flanked by the same restriction sites. Such an engineered library is non-naturally occurring.

As used herein, the term "coding sequence" or "CDS" refers to a nucleic acid that contains genetic information encoding a polypeptide, protein, or untranslated RNA (e.g., rRNA, tRNA, anti-sense RNA). Additional elements such as promoter, terminator, 5' untranslated region (UTR), and 3' UTR may be needed for the transcription and/or translation of the coding sequence.

As used herein, the term "promoter" refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. A promoter may be constitutively active ("constitutive promoter") or be controlled by other factors such as a chemical, heat or light. The activity of an "inducible promoter" is induced by the presence or absence or biotic or abiotic factors. Commonly used constitutive promoters include CMV, EF1a, SV40, PGK1, Ubc, human beta actin, CAG, Ac5, Polyhedrin, TEF1, GDS, ADH1 (repressed by ethanol), CaMV35S, Ubi, H1, U6, T7 (requires T7 RNA polymerase), and SP6 (requires SP6 RNA polymerase). Common inducible promoters include TRE (inducible by Tetracycline or its derivatives; repressible by TetR repressor), GAL1 & GAL10 (inducible with galactose; repressible with glucose), lac (constitutive in the absence of lac repressor (LacI); can be induced by IPTG or lactose), T7lac (hybrid of T7 and lac; requires T7 RNA polymerase which is also controlled by lac operator; can be induced by IPTG or lactose), araBAD (inducible by arabinose which binds repressor AraC to switch it to activate transcription; repressed catabolite repression in the presence of glucose via the CAP binding site or by competitive binding of the anti-inducer fucose), trp (repressible by tryptophan upon binding with TrpR repressor), tac (hybrid of lac and trp; regulated like the lac promoter; e.g., tacI and tacII), and pL (temperature regulated). The promoter can be a prokaryotic or eukaryotic promoter, depending on the host. Common promoters and their sequences are well known in the art.

One should appreciate that promoters have modular architecture and that the modular architecture may be altered. Bacterial promoters typically include a core promoter element and additional promoter elements. The core promoter refers to the minimal portion of the promoter required to initiate transcription. A core promoter includes a Transcription Start Site, a binding site for RNA polymerases and general transcription factor binding sites. The "transcription start site" refers to the first nucleotide to be transcribed and is designated +1. Nucleotides downstream of the start site are numbered +1, +2, etc., and nucleotides upstream of the start site are numbered −1, −2, etc. Additional promoter elements are located 5' (i.e., typically 30-250 bp upstream of the start site) of the core promoter and regulate the frequency of the transcription. The proximal promoter elements and the distal promoter elements constitute specific transcription factor site. In prokaryotes, a core promoter usually includes two consensus sequences, a −10 sequence or a −35 sequence, which are recognized by sigma factors. The −10 sequence (10 bp upstream from the first transcribed nucleotide) is typically about 6 nucleotides in length and is typically made up of the nucleotides adenosine and thymidine (also known as the Pribnow box). The presence of this box is essential to the start of the transcription. The −35 sequence of a core promoter is typically about 6 nucleotides in length. The nucleotide sequence of the −35 sequence is typically made up of the each of the four nucleosides. The presence of this sequence allows a very high transcription rate. In some embodiments, the −10 and the −35 sequences are spaced by about 17 nucleotides. Eukaryotic promoters are more diverse than prokaryotic promoters and may be located several kilobases upstream of the transcription starting site. Some eukaryotic promoters contain a TATA box, which is located typically within 40 to 120 bases of the transcriptional start site. One or more upstream activation sequences (UAS), which are recognized by specific binding proteins can act as activators of the transcription. Theses UAS sequences are typically found upstream of the transcription initiation site. The distance between the UAS sequences and the TATA box is highly variable and may be up to 1 kb.

"Untranslated region" or "UTR" refers to either section of the untranslated portion in an mRNA molecule that is located at the 5' side ("5' UTR") or 3' side ("3' UTR") of a coding sequence. The 5' UTR contains a sequence that is recognized by the ribosome which allows the ribosome to bind and initiate translation ("ribosome binding site" or "RBS"). The 3' UTR is involved in translation termination as well as post transcriptional gene expression.

"Terminator" refers to a nucleic acid sequence that hinders or stops transcription of a RNA polymerase. Generally a self-annealing hairpin structure may be formed on the elongating transcript, which results in the disruption of the mRNA-DNA-RNA polymerase ternary complex. The natural terminator sequence contains a 20 base pair GC-rich region of dyad symmetry followed by a short poly-T tract which is transcribed to RNA to form the terminating hairpin and a 7-9 nucleotide "U track" respectively. (Dyad symmetry refers generally to two areas of a DNA strand whose base pair sequences are inverted repeats of each other. They are often described as palindromes.) A survey of natural and synthetic terminators is provided in Chen et al., Characterization of 582 natural and synthetic terminators and quantification of their design constraints, Nature Methods 10, 659-664 (2013), incorporated herein by reference.

As used herein, the term "vector" refers to any genetic element, such as a plasmid, phage, transposon, cosmid, chromosome, artificial chromosome, episome, virus, virion, etc., capable of replication when associated with the proper control elements and which can transfer gene sequences into or between cells. The vector may contain a selection module suitable for use in the identification of transformed or transfected cells. For example, selection modules may provide antibiotic resistant, fluorescent, enzymatic, as well as other traits. As a second example, selection modules may complement auxotrophic deficiencies or supply critical nutrients not in the culture media. Types of vectors include cloning and expression vectors. As used herein, the term "cloning vector" refers to a plasmid or phage DNA or other DNA sequence which is able to replicate autonomously in a host cell and which is characterized by one or a small number of restriction endonuclease recognition sites and/or sites for site-specific recombination. A foreign DNA fragment may be spliced into the vector at these sites in order to bring about the replication and cloning of the fragment. The term "expression vector" refers to a vector which is capable of expressing of a gene that has been cloned into it. Such expression can occur after transformation into a host cell, or in an in vitro system. The cloned DNA is usually operably linked to one or more regulatory sequences, such as promoters, activator/repressor binding sites, terminators, enhancers and the like. The promoter sequences can be constitutive, inducible and/or repressible.

A vector used in assembly of stage 1 constructs is referred to as a "stage 1 vector" in some embodiments. A vector used in assembly of stage 2 constructs is referred to as a "stage 2 vector" in some embodiments.

As used herein, unless otherwise stated, the term "transcription" refers to the synthesis of RNA from a DNA template; the term "translation" refers to the synthesis of a polypeptide from an mRNA template. Translation in general is regulated by the sequence and structure of the 5' untranslated region (5'-UTR) of the mRNA transcript. One regulatory sequence is the ribosome binding site (RBS), which promotes efficient and accurate translation of mRNA. The prokaryotic RBS is the Shine-Dalgarno sequence, a purine-rich sequence of 5'-UTR that is complementary to the UCCU core sequence of the 3'-end of 16S rRNA (located within the 30S small ribosomal subunit). Various Shine-Dalgarno sequences have been found in prokaryotic mRNAs and generally lie about 10 nucleotides upstream from the AUG start codon. Activity of a RBS can be influenced by the length and nucleotide composition of the spacer separating the RBS and the initiator AUG. In eukaryotes, the Kozak sequence lies within a short 5' untranslated region and directs translation of mRNA. An mRNA lacking the Kozak consensus sequence may also be translated efficiently in an in vitro system if it possesses a moderately long 5'-UTR that lacks stable secondary structure. While E. coli ribosome preferentially recognizes the Shine-Dalgarno sequence, eukaryotic ribosomes (such as those found in retic lysate) can efficiently use either the Shine-Dalgarno or the Kozak ribosomal binding sites.

"Type IIs enzyme" refers to restriction endonucleases that recognize a double-stranded DNA at a specific sequence ("restriction site" or "recognition site") and cleave the double-stranded DNA at a cleavage site that is outside the recognition site on the double-stranded DNA. Generally overhangs of from 3 to 6 nucleotides are produced upon type IIs restriction. A selection of such enzymes is provided on the REBASE webpage (rebase.neb.com/cqi-bin/asvmmlist) and in the review of Szybalsky et at, 1991, Gene, 100:13-26. Examples include but are not limited to BstF5I, BtsCI, BsrDI, BtsI, AlwI, BccI, BsmAI, EarI, PleI, BmrI, BsaI, BsmBI, FauI, MnlI, SapI, BbsI, BciVI, HphI, MboII, BfuAI, BspCNI, BspMI, SfaNI, HgaI, BseRI, BbvI, EciI, FokI, BceAI, BsmFI, BtgZI, BpuEI, BsgI, MmeI, BseGI, Bse3DI, BseMI, AclWI, Alw26I, Bst6I, BstMAI, Eam1104I, Ksp6321, PpsI, BfiI, Bso31I, BspTNI, Eco31I, Esp3I, SmuI, BfuI, BpiI, BpuAI, BstV2I, AsuHPI, Acc361, LweI, AarI, BseMII, TspDTI, TspGWI, BseXI, BstV1I, Eco571, Eco57MI, GsuI, and BcgI. Those listed on pages 12-13, Table 1 and Table 2 of U.S. Publication No. 20130267021 are non-exclusive examples and are incorporated herein by reference.

As used herein, the term "host" or "host cell" refers to any prokaryotic or eukaryotic single cell (e.g., yeast, bacterial, archaeal, etc.) cell or organism. The host cell can be a recipient of a replicable expression vector, cloning vector or any heterologous nucleic acid molecule. Host cells may be prokaryotic cells such as species of the genus Escherichia or Lactobacillus, or eukaryotic single cell organism such as yeast. The heterologous nucleic acid molecule may contain, but is not limited to, a sequence of interest, a transcriptional regulatory sequence (such as a promoter, enhancer, repressor, and the like) and/or an origin of replication. As used herein, the terms "host," "host cell," "recombinant host" and "recombinant host cell" may be used interchangeably. For examples of such hosts, see Green & Sambrook, 2012, Molecular Cloning: A laboratory manual, 4th ed., Cold Spring Harbor Laboratory Press, New York, incorporated herein by reference.

One or more nucleic acid sequences can be targeted for delivery to target prokaryotic or eukaryotic cells via conventional transformation techniques. As used herein, the term "transformation" is intended to refer to a variety of art-recognized techniques for introducing an exogenous nucleic acid sequence (e.g., DNA) into a target cell, including calcium phosphate or calcium chloride co-precipitation, conjugation, electroporation, sonoporation, optoporation, injection and the like. Suitable transformation media include, but are not limited to, water, $CaCl_2$, cationic polymers, lipids, and the like. Suitable materials and methods for transforming target cells can be found in Green & Sambrook, 2012, Molecular Cloning: A laboratory manual, 4th ed, Cold Spring Harbor Laboratory Press, New York, incorporated herein by reference, and other laboratory manuals.

As used herein, the term "selectable marker" or "reporter" refers to a gene, operon, or protein that upon expression in a host cell or organism, can confer certain characteristics that can be relatively easily selected, identified and/or measured. Reporter genes are often used as an indication of whether a certain gene has been introduced into or expressed in the host cell or organism. Examples of commonly used reporters include: antibiotic resistance ("abR") genes, fluorescent proteins, auxotropic selection modules, β-galactosidase (encoded by the bacterial gene lacZ), luciferase (from lightning bugs), chloramphenicol acetyltransferase (CAT; from bacteria), GUS (β-glucuronidase; commonly used in plants) green fluorescent protein (GFP; from jelly fish), and red fluorescent protein (RFP). Typically host cells expressing the selectable marker are protected from a selective agent that is toxic or inhibitory to cell growth.

The term "engineer," "engineering" or "engineered," as used herein, refers to genetic manipulation or modification of biomolecules such as DNA, RNA and/or protein, or like technique commonly known in the biotechnology art.

Other terms used in the fields of recombinant nucleic acid technology and molecular and cell biology as used herein will be generally understood by one of ordinary skill in the applicable arts.

Assembly Method and Kit

Methods and kits for rapidly assembling pre-made DNA modules are described herein to run rapid (e.g., 8 hours or less) prototyping in vitro and systemically enable in vivo testing using the existing DNA pieces. In some embodiments, the method is also referred to as "Iterative Assembly" or "Idiotproof Assembly." The method can use modular components, sometimes referred to as Iterative Assembly_

Figure 2A:
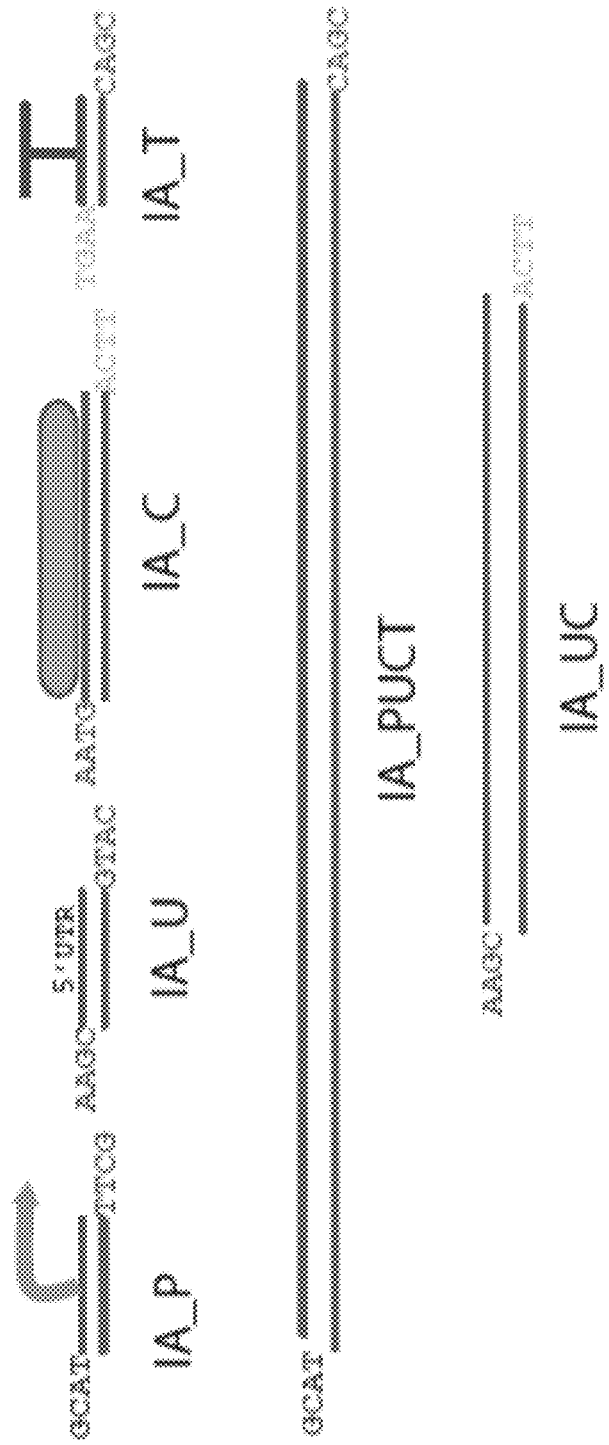
FIG. 2A illustrates exemplary stage 0 pieces/genetic modules and their pre-designed cohesive ends that dictate the assembly order of PUCT.

Promoter (IA_P), IA_Untranslated Region (IA_UTR), IA_Coding Sequence (IA_CDS), IA_terminator (IA_T), and IA_vector (IA_V). There are also variants of these modules, such as IA_PUCT (a combination of all modules) and IA_UC (a combination of UTR and CDS). Variations of the modules can be used for DNA modules that do not fit the mold of a traditional IA_P, IA_U, IA_C, or IA_T. For example, a random spacer may be implemented as IA_PUCT while a RNA-based activator as IA_UC. An example of these pieces can be found under FIG. 2A, which are also referred to as "stage 0 pieces" in some embodiments. It should be noted that exemplary cohesive ends are shown in FIG. 2A for each piece to illustrate the design in which the identity of the cohesive ends dictate the order of assemble, IA_P followed by IA_U, then IA_C and IA_T. Other cohesive ends of different length and/or sequence can also be used. In the case of a 4-nucleotide cohesive end, 4^4=256 different cohesive ends are available.

Figure 2B:
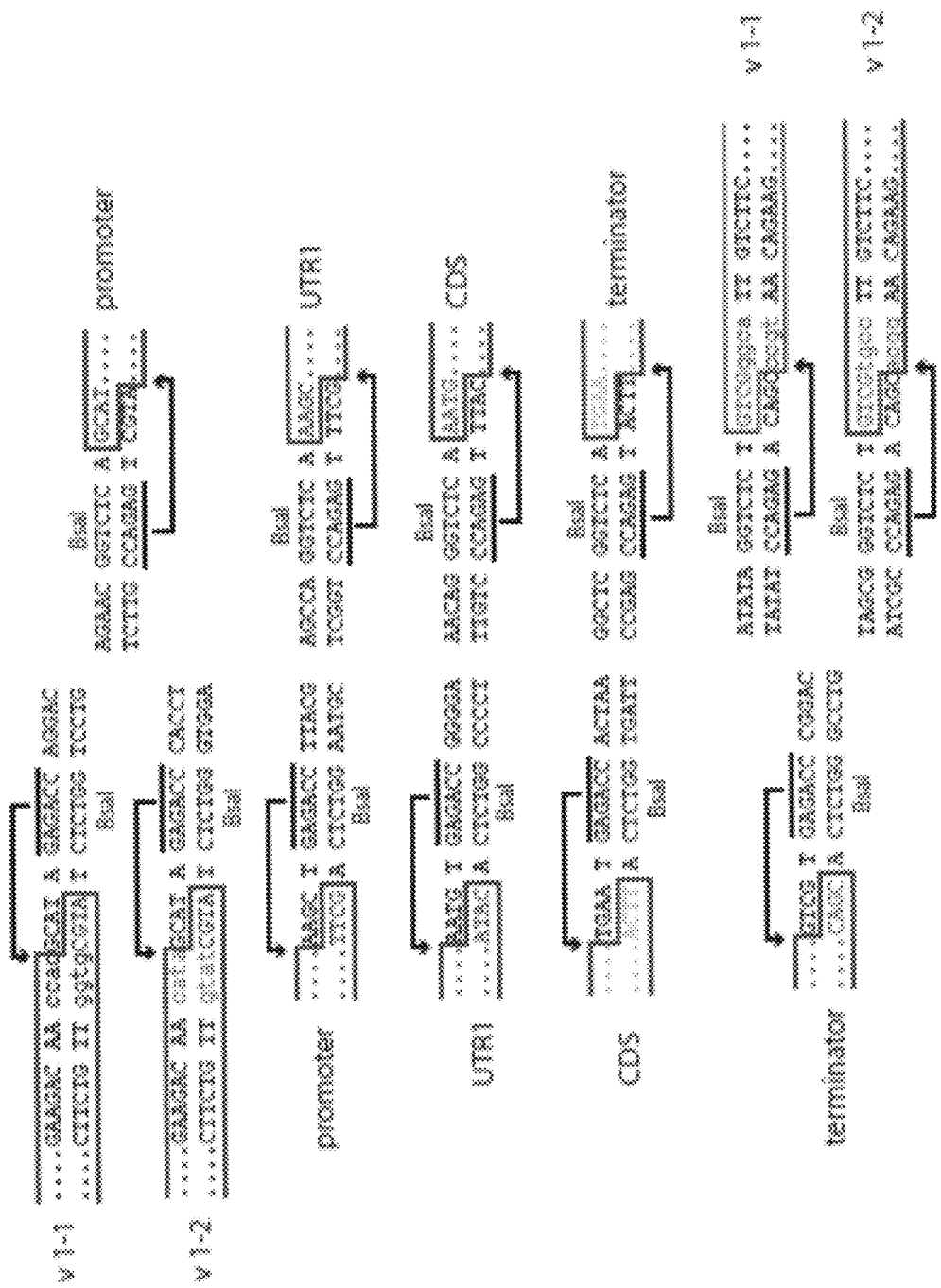
FIG. 2B illustrates exemplary cloning ends of stage 0 pieces for assembly into stage 1 vectors v1-1 and v1-2.

IA_P, IA_U, IA_C, IA_T, or a combination thereof may be assembled in a predetermined order by having predefined cloning ends attached or engineered to 5' and/or 3' ends. One exemplary set of cloning ends are illustrated in FIG. 2B and listed below (only top strand sequences are shown below since bottom strands are complementary to top strands).

| SEQ ID No. | Cloning End | Top Strand Sequence |
|---|---|---|
| 1 | v1-1, 3' end | GAAGACAACCACGCATAGAGACCAGGAC |
| 2 | V1-2, 3' end | GAAGACAACATAGCATAGAGACCCACCT |
| 3 | Promoter, 5' end | AGAACGGTCTCAGCAT |
| 4 | Promoter, 3' end | AAGCTGAGACCTTACG |
| 5 | UTR1, 5' end | AGCCAGGTCTCAAAGC |
| 6 | UTR1, 3' end | AATGTGAGACCGGGGA |
| 7 | CDS, 5' end | AACAGGGTCTCAAATG |
| 8 | CDS, 3' end | TGAATGAGACCACTAA |
| 9 | Terminator, 5' end | GGCTCGGTCTCATGAA |
| 10 | Terminator, 3' end | GTCGTGAGACCCGGAC |
| 11 | v1-1, 5' end | ATATAGGTCTCTGTCGGGCATTGTCTTC |
| 12 | v1-2, 5' end | TAGCGGGTCTCTGTCGTGCCTTGTCTTC |

The above sequences are for illustration purpose only. It should be noted that the sequence of the cloning ends for any genetic module can be varied, e.g., by replacing the BsaI and/or BbsI recognition sites with other Type IIs enzyme sites, and/or replacing the spacer sequence located between the Type IIs enzyme recognition site and cleavage site with any sequence (e.g., degenerate sequence). Suitable Type IIs enzymes include but are not limited to BsaI, Eco31I, BspTN1, Bso31I, BbsI, BpuAI, BpiI, BstV21, BsmBI, Esp3I, FokI, AlwI, and BfiII.

While the identity of the cloning ends can vary, the cohesive ends generated by Type IIs enzyme digestion must be designed in a way such that each module can only fit in a certain position in the assembled product. In other words, it is important that only an IA_P can anneal to an IA_U, an IA_C to an IA_T (and not an IA_P to an IA_T), or any other order that ensures that the genetic modules are operably linked to one another to allow, e.g., transcription and/or translation. However, the ends can use any ligation method provided the previous statement holds true. In the example shown in FIG. 2B, the Type IIs BsaI enzyme is used (recognition sites are indicated by solid lines and cleavage sites are indicated by arrows) and Golden Gate Assembly is conducted; the IA_P to IA_U linker is AAGC, IA_U to IA_C is AATG, IA_C to IA_T is TGAA, IA_V to IA_P is GCAT, and IA_T to IA_V is GTCG. Any other Type IIs enzyme can be used in lieu of BasI.

In some embodiments, compatible cohesive ends that anneal with each other can be assembled together using Golden Gate Assembly, as disclosed by Engler et al., *PLoS One*, 4(5), e5553, incorporated herein by reference in its entirety.

Per module, there can be many IA_P, IA_U, IA_C, IA_T and IA_V stage 0 pieces. These can be collected in a library for future use. In some embodiments, the library can be stored in multi-well plates and can be used as part of a kit for rapid in vitro assembly of desirable transcription units or genetic circuits. As of April 2016, there are 96 IA_P modules, 48 IA_U modules, 99 IA_C modules, 22 IA_T modules in a custom library made. Each one of these modules can be combined to one another, thereby giving 96*48*99*22=10 million combinations, each a transcription unit. Stage 0 pieces can be engineered to have predefined cloning ends (e.g., those in FIG. 2B), which can either be added on by polymerase chain reaction or can be put in by cloning into a predefined vector.

Each IA_P, IA_U, IA_C, and IA_T can be assembled with a vector, IA_V. As shown in FIG. 2B, 2 different vectors (v1-1 and v1-2) having different origin of replication and/or selectable marker can be used. As of April 2016, a total of 49 vectors have been made in a custom library. The vectors are chosen to facilitate end in vivo testing (stage 1 vectors and stage 2 vectors discussed in more detail hereunder). The speed of running in vitro partially comes from the ability to reuse modules and from mixing and matching modules.

Figure 3A:
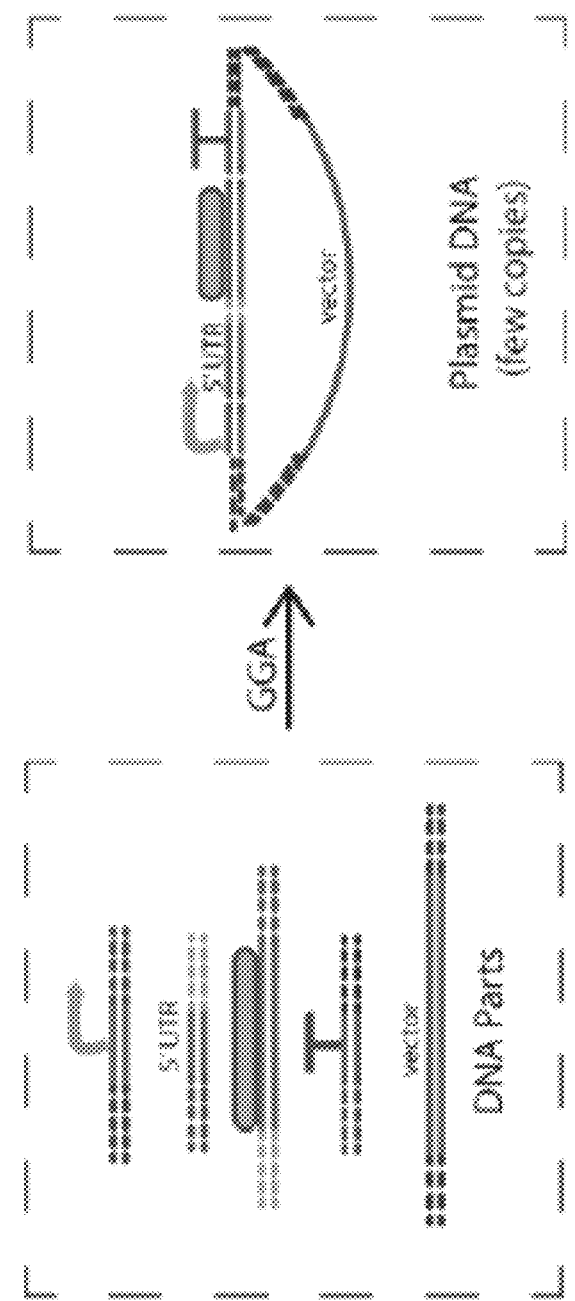
FIG. 3A illustrates an exemplary workflow of assembling modular components into a plasmid.
Figure 3B:
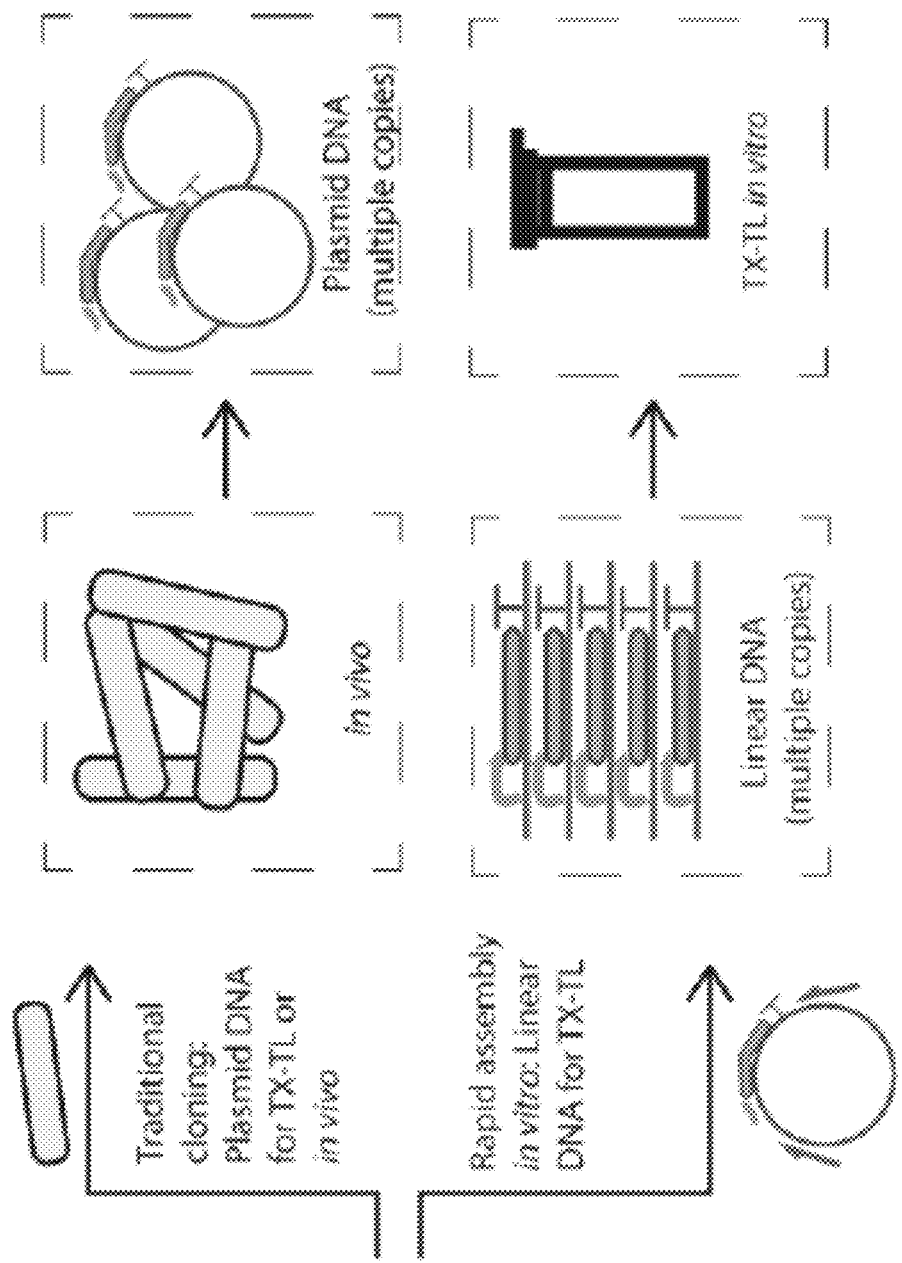
FIG. 3B illustrates the different workflow, from an assembled plasmid from FIG. 3A, between traditional cloning and rapid assembly in vitro.

FIGS. 3A-3B demonstrate an exemplary general workflow. Referring to FIG. 3A, the assembly procedure proceeds by, e.g., standard Golden Gate Assembly (GGA) to a predefined vector, which creates minimal amounts of plasmid DNA copies. The ligation is a 1-pot ligation, e.g., all pieces (not pre-digested) can be added in and digestion and ligation will occur within the reaction. This plasmid DNA can then be transformed to prepare for in vivo testing as well as used after a PCR reaction to conduct in vitro testing, as shown in FIG. 3B.

Figure 3C:
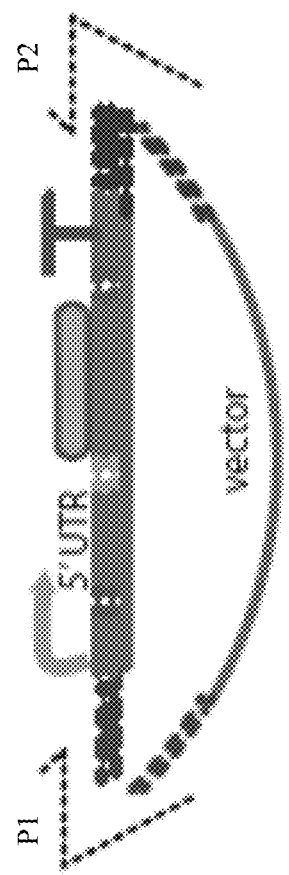
FIG. 3C illustrates an exemplary PCR strategy using specially designed primers to selectively amplify correctly assembled plasmid from FIG. 3A to prepare linear DNA for TX-TL.

For the in vitro testing, after the assembly reaction linear DNA can be made (FIG. 3C). Two primers P1 and P2 can be designed such that each partially binds to the vector at one portion and partially to the promoter/terminator at another portion (overlap primers), each portion with a melting temperature (Tm)<40° C., but both portions together provide a total Tm of about 55-65° C., about 58-62° C. or about 60° C. It is designed this way to enforce enrichment of correctly cloned constructs, and provides a correctly-sized linear DNA which can be then be run in TX-TL. If a construct is not correctly cloned (e.g., IA_V does not ligate to IA_P and/or IA_T does not ligate to IA_V), one primer will bind with a low Tm and will fail the PCR. Once a linear DNA is enriched, it can then be run in TX-TL with the support of gamS protein to block exonuclease activity.

Although one can use non-overlap primers to amplify the linear DNA to test by designing primers to bind to vectors only, this alternative approach will also amplify the case where the vector self-ligates (without ligating with the genetic modules) or the genetic modules do not anneal in the desired correct order. Therefore, the use of non-overlap primers may result in poor selection of the correct linear DNA cassette. Using overlap primers as described herein is especially critical when multiple ligation reactions are required where the ligation efficiency may be low.

Linear DNA produced by PCR may not be completely of correct sequence identity due to mutations introduced during the PCR amplification steps or during the digestion and ligation step. However, this can be mitigated by the fact that the linear DNA can be run in an in vitro transcription-translation system in non-clonal form, as there is no requirement to provide clonal DNA in the in vitro expression reaction.

If running a plasmid is desired in lieu of running a linear DNA, one can follow the "Traditional Cloning" workflow in FIG. 3B to purify plasmid which can be sequence or size verified and run in TX-TL.

Figure 4A:
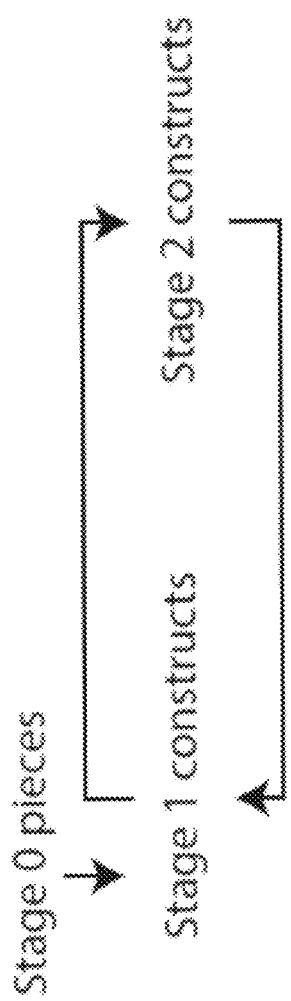
FIG. 4A illustrates an exemplary workflow from stage 0 pieces to stage 1 constructs, and the cycling between stage 1 and stage 2 constructs.
Figure 4B:
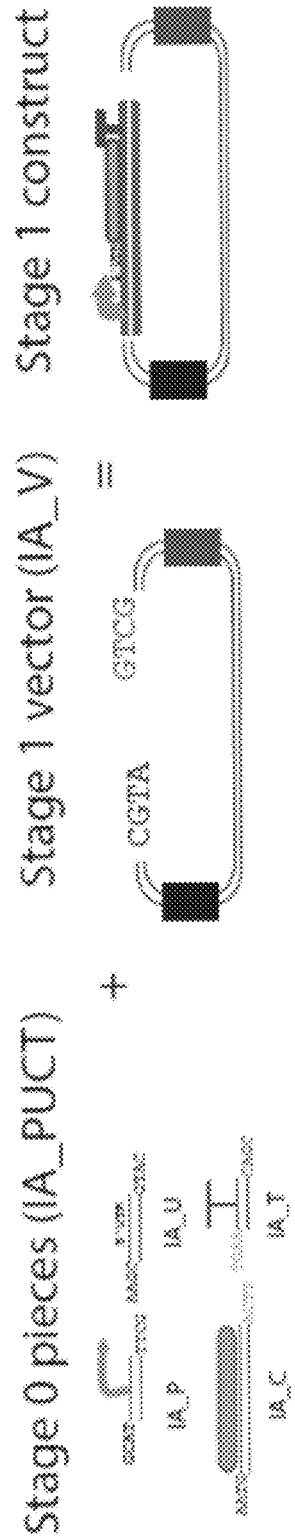
FIG. 4B illustrates, in one embodiment, the assembly of stage 0 pieces with stage 1 vector into stage 1 construct.

A challenge for transitioning large circuits from in vitro to in vivo is the difficulty in consolidating all pieces onto vivo compatible plasmids. Using the method described here, this consolidation is extremely easy and requires little to no DNA design. Once stage 0 pieces are determined they can be cloned into different IA_V to produce stage 1 constructs that can be already ready for vivo expression or can be cycled to make stage 2 constructs (FIG. 4A). Stage 1 vectors can be the same vectors used to produce the rapid linear DNA from FIG. 3C. An example of the production of the stage 1 construct from stage 0 pieces and a stage 1 vector is given in FIG. 4B.

Figure 4C:
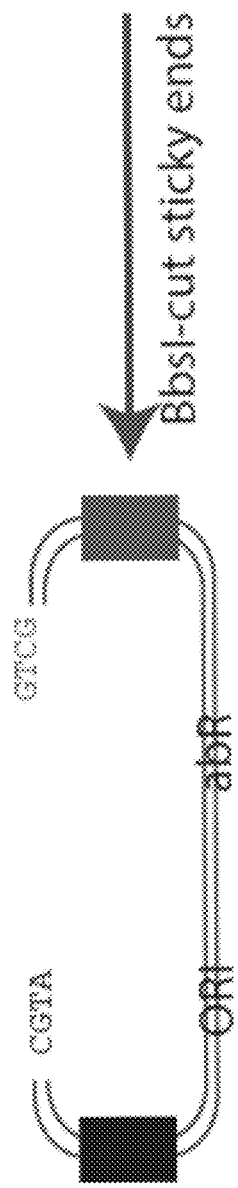
FIG. 4C illustrates exemplary swappable areas on stage 1 vector to ensure in vivo compatibility.

FIG. 4C shows that the stage 1 vectors can have swappable areas to ensure in vivo compatibility. In particular, the origin of replications (ORIs) can be swapped and the antibiotic resistance markers (abR) can be swapped to those commonly used. Any origins of replication commonly used in molecular cloning may be used, such as colE1, pSC101, p15A, pBBR1, pMB1 and R6K. The antibiotic resistance marker can be any marker commonly used in molecular cloning, such as AmpR/CarbR (ampicillin/carbenicillin resistance), KanR (kanamycin resistance), CmR (chloramphenicol resistance), ZeoR (zeocin resistance), TetR (tetracycline resistance), SpecR (spectinomycin resistance), StrepR (streptomycin resistance), NeoR (neomycin resistance), and BleR (bleomycin resistance). Different vectors having different ORI and/or abR can be pre-made and collected in a custom library.

Figure 4D:
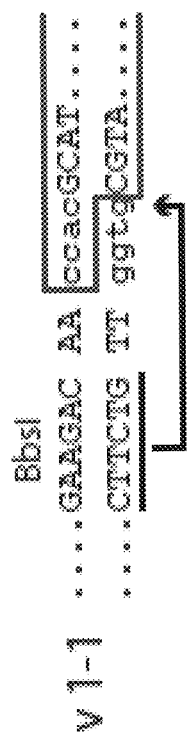
FIG. 4D illustrates an exemplary sticky end for a stage 1 vector.

Additionally, there are sticky ends (solid boxes) engineered in the vectors that, in the example shown in FIG. 4C, are cut with a different enzyme than the stage 0 to stage 1 transition (e.g., BbsI instead of BsaI). An exemplary DNA sequence (top strand: GAAGACAACCACGCAT (SEQ ID No.: 13) and sticky end for BbsI digestion and ligation in vector v1-1 are shown in FIG. 4D.

Figure 4E:
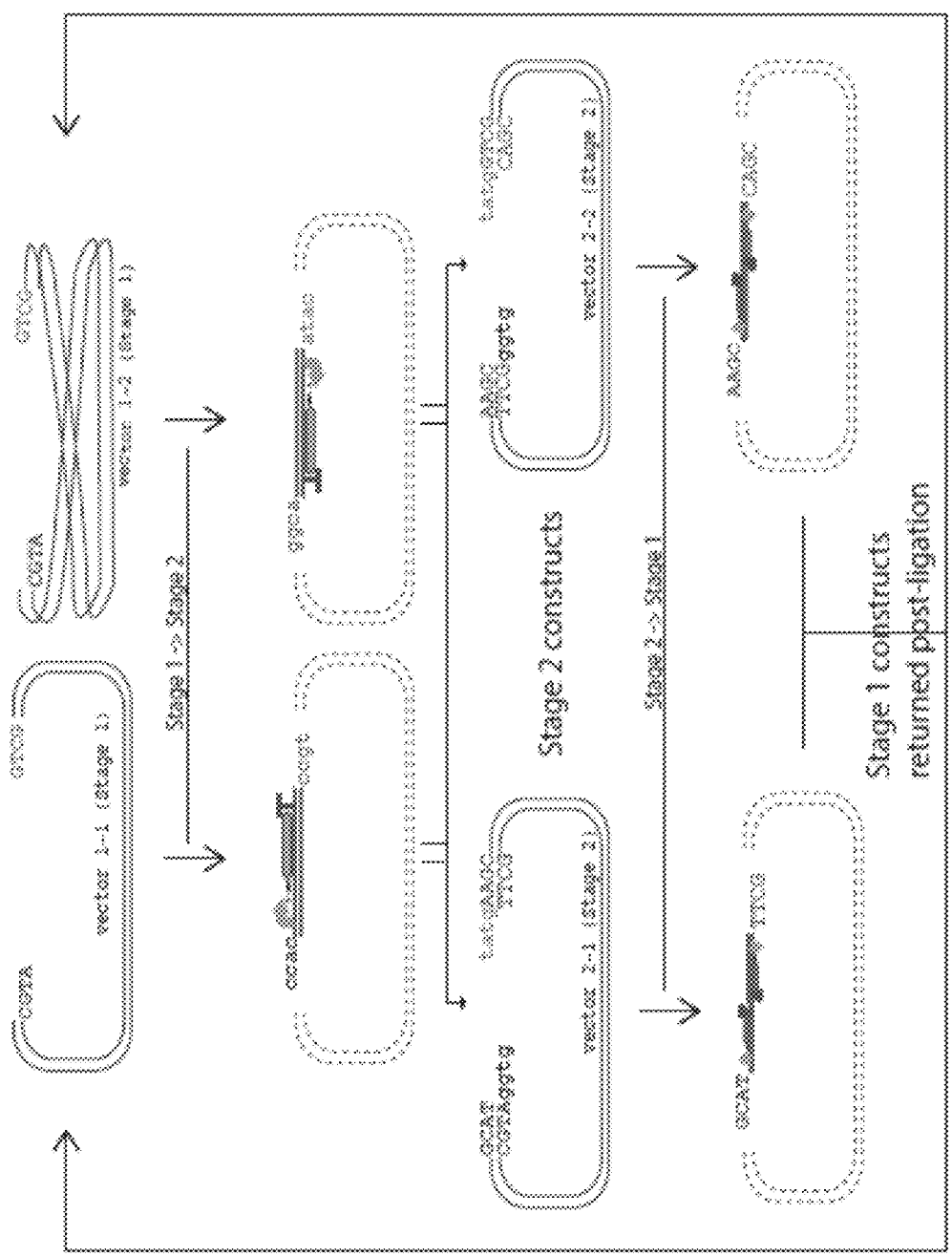
FIG. 4E illustrates an exemplary cycling between stage 2 and stage 1 indefinitely with set vectors.
Figure 6A:
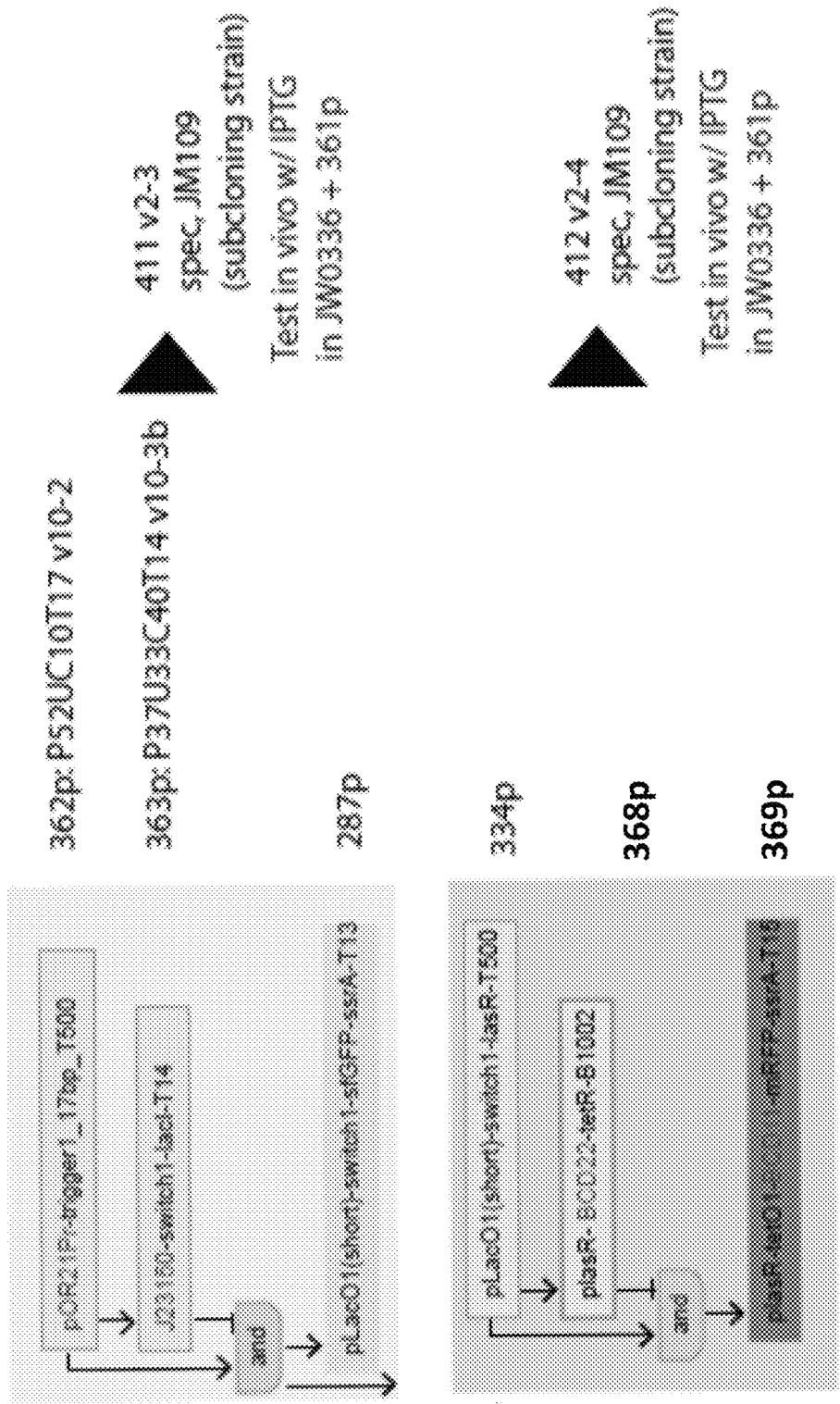
FIGS. 6A-6C illustrate, in one embodiment, assembly and cloning of two variants of a 6-piece nested feed-forward loop.
Figure 6B:
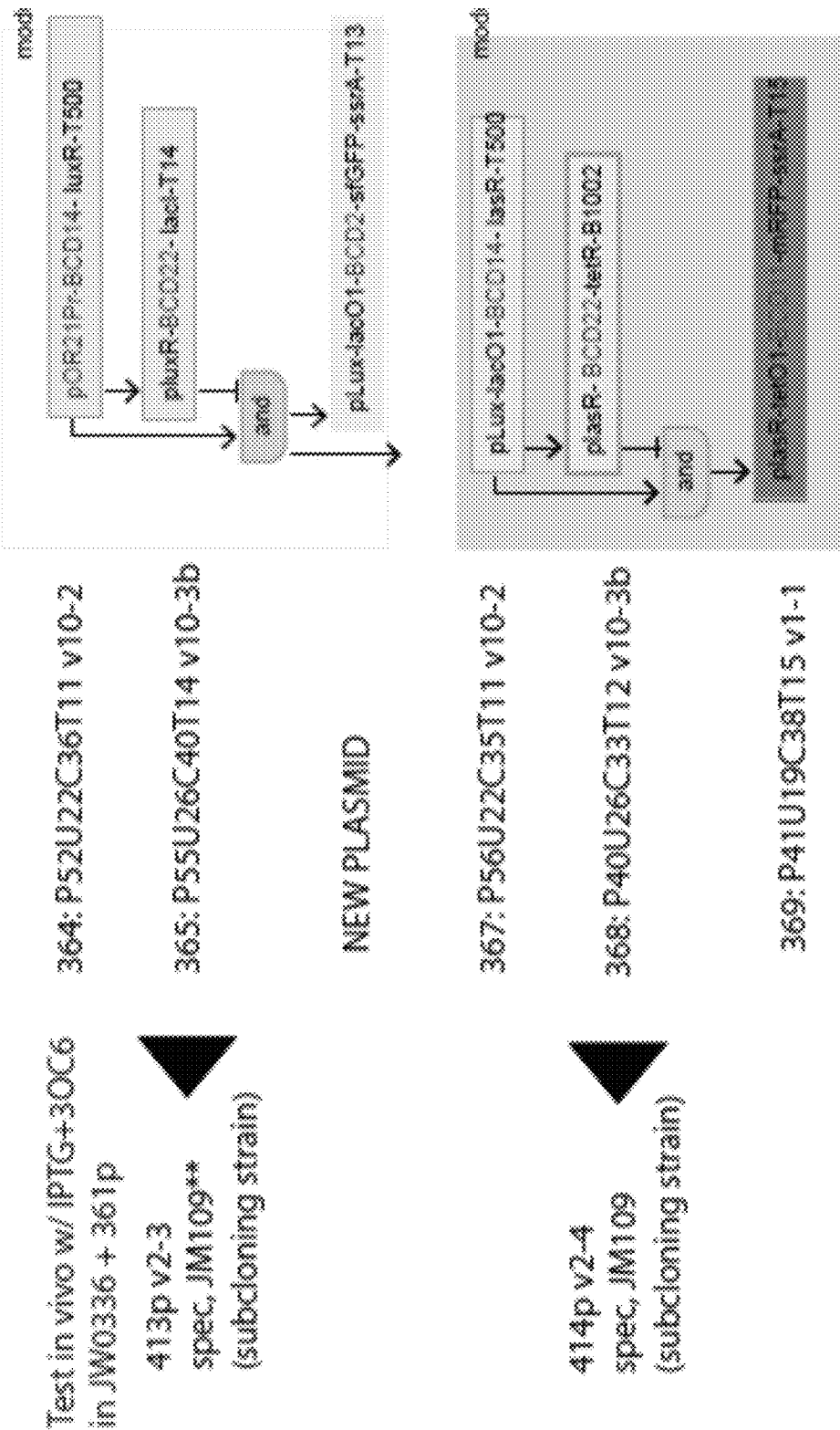
Figure 6C:
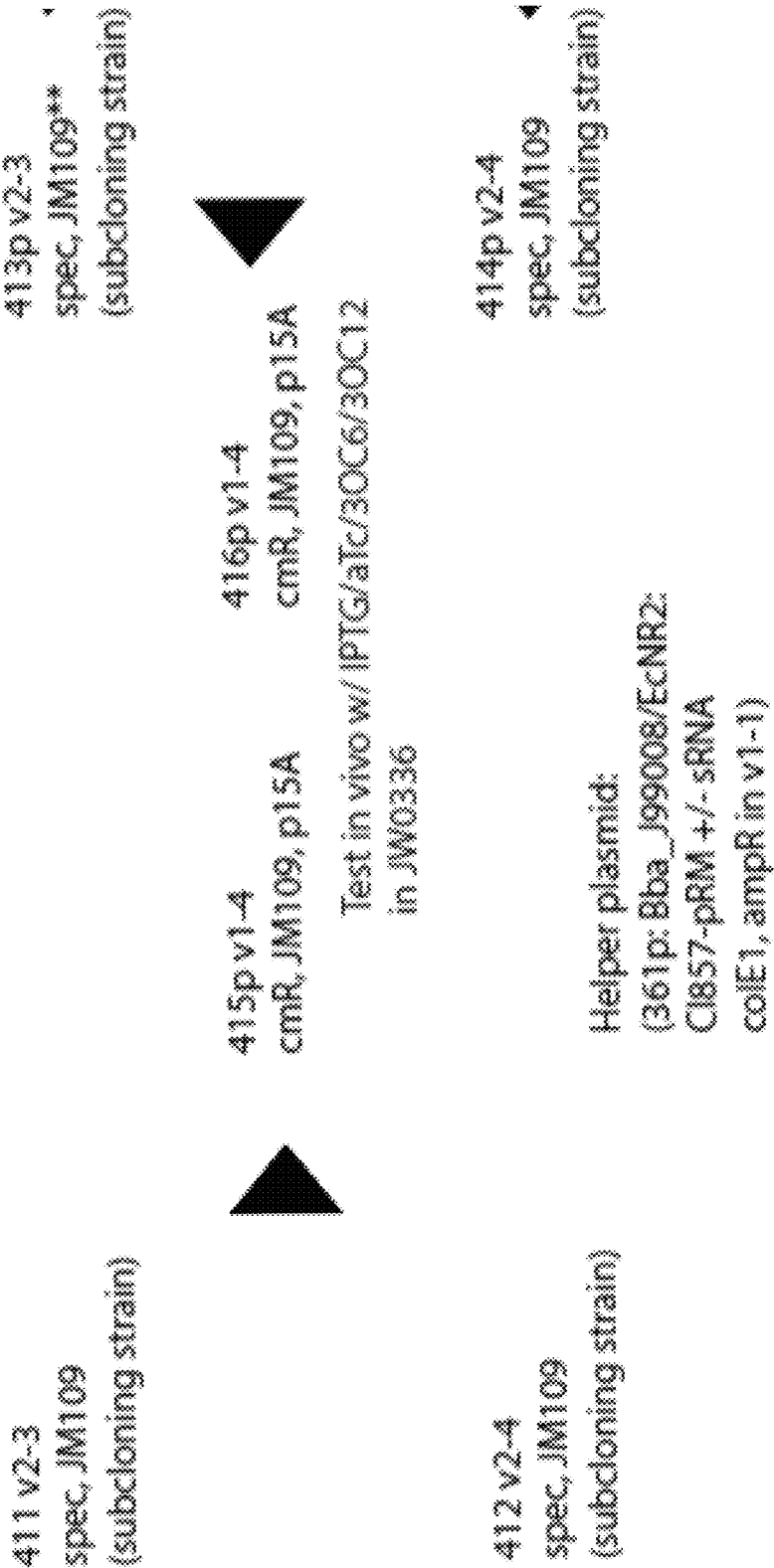

FIG. 4E then demonstrates the cycling ability between stage 1 pieces and stage 2 pieces. While FIG. 4E illustrates a 2 piece to 1 piece assembly, one can also go from multiple pieces (e.g., 3, 4, 5, 6, 7, 8, 9 or more) to 1 piece. In this example, 2 PUCT transcription units (stage 0 pieces) are put into two different stage 1 vectors with BsaI digestion, v1-1 and v1-2, to make stage 1 constructs. These stage 1 constructs have compatible ends with each other, and can be directly put into a one-pot assembly with a stage 2 vector (v2-1 or v2-2 in this case) to form stage 2 constructs when cut with BbsI. Note here each stage 2 construct has 2 PUCT transcription units (not shown). In this case, both stage 2 constructs can regenerate stage 1 constructs by another one-pot assembly with a recycled stage 1 vector (v1-1 or v1-2) using BsaI digestion. Then, by going through 3 cycles of assembly (1 cycle of stage 0 to stage 1, 1 cycle of stage 1 to stage 2, and 1 cycle of stage 2 to stage 1) one can make up to 8 PUCT transcription units. FIGS. 6A-6C show this strategy in one specific example, aiming to combine 2×6 PUCT expressible units into 2 plasmids for in vivo expression, as explained in more detail below.

FIG. 4E also demonstrates that the orientation of the PUCT transcription units can be varied depending on the needs of the final product and the stability of the DNA. In this example, v1-2 is designed to flip the orientation of the second PUCT unit relative to the first PUCT unit (e.g., divergent orientation). However, the PUCT unit can be engineered to be convergent or divergent. In some embodiments, multiple inverted repeats or repeated DNA segments may cause hairpins upon plasmid propagation in vivo and subsequent deletions, which may require convergent or divergent assembly. In certain embodiments, it may also be desirable to choose different assembly directions to influence transcriptional strength of the resulting PUCT unit due to secondary structure or context effects.

Note that as long as DNA originates in plasmid form, it has been found that sequencing of the constructs is not required. The product if verified to be of the correct size from one stage can go directly into the latter stage. If the DNA originates in linear form or is formed from synthetic DNA, sequencing can be optionally used to rule out mutations introduced by the DNA polymerase amplification step.

Figure 5A:
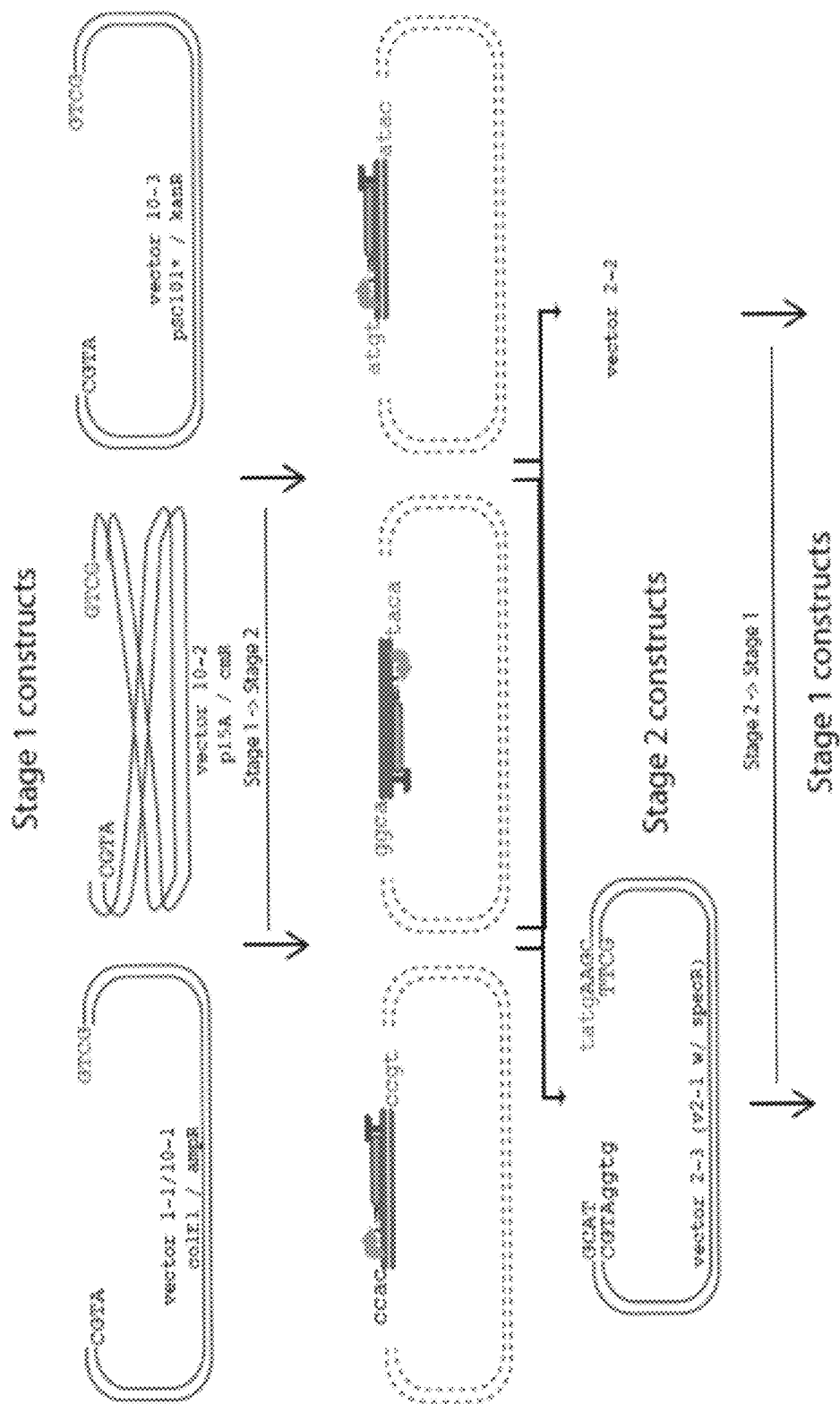
FIG. 5A illustrates an exemplary assembly strategy of 3 transcription units in 3 separate plasmids (each having different antibiotic resistance markers and/or origins of replication), with possibility of cycling to combine all 3 to 1 stage 2 plasmid and further cycling (not shown).

FIG. 5A shows another exemplary layout, where 3 PUCT transcription units are cloned into 3 separate stage 1 plasmids to make stage 1 constructs which are in vivo compatible (e.g., colE1/ampR, p15A/cmR, pSC101*/kanR). These plasmids can then be tested immediately in TX-TL or in vivo. If combining them onto 1 plasmid is desired, the plasmids can be assembled in a one-pot reaction with, e.g., BbsI to make a stage 2 construct which has all 3 PUCT transcription units in 1 plasmid. This again can be tested in TX-TL or in vivo.

Figure 5B:
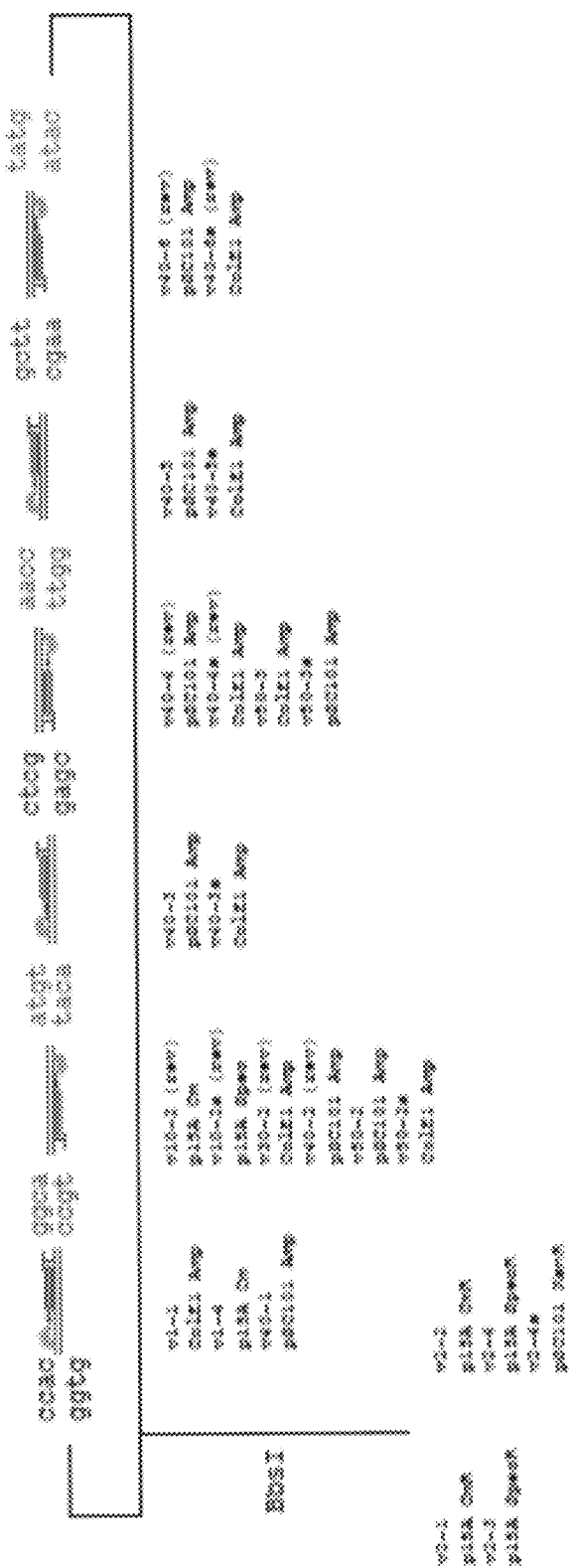
FIG. 5B illustrates an exemplary assembly strategy of 6 transcription units (from 6 stage 1 constructs) into 1 stage 2 plasmid. Further cycling is possible but not shown.

FIG. 5B shows another exemplary layout, where 6 PUCT transcription units, from 6 separate stage 1 vectors, are cloned into a stage 2 construct (using stage 2 vectors, e.g., v2-1, v2-2, v2-3, v2-4, v2-4a). ORI and abR are shown for each stage 2 vector. Generally it is impossible to express 6 separate plasmids in vivo since the maximum compatibility of host cells typically only allows for 3 plasmids. Here, it is shown in FIG. 5B that each stage 1 vector can be different (with different ORI and/or abR as shown), as long as the sticky ends are conserved. Again, the sticky ends are for illustration purpose only and different sequences can be used. The destination stage 2 vector can also be varied depending on the need (e.g., low copy/medium copy plasmid or different antibiotic resistance marker).

It is noted in the exemplary layout of FIG. 5B that by designating different options for each stage 1 vector, one can expedite consolidating multiple PUCT transcription units into one unit without the need to conduct significant re-engineering and cloning. For example, if it is desired to produce a circuit using 6 PUCT units to be tested in combinations in vivo and then combined into one unit, vectors can be chosen such that the stage 1 constructs are individually compatible for testing (e.g., having compatible OR1 and/or abR, such as colE1 AmpR and P15A CmR, to co-transform and test). In addition, the stage 2 vector can be chosen from a family of vectors (e.g., from a premade library), depending on the need for the final testing environment (e.g., low-copy or high-copy number, and/or certain origin of replication to be compatible with an additional plasmid to be co-transformed).

In some cases, the post-cloned PUCT in a stage 1 or stage 2 vector may be toxic to the cell at high copy number or high expression level, and produce a subsequent deletion of a regulatory region (e.g., promoter, UTR) after propagation in vivo. Thus, in certain embodiments, a different vector may be selected with different copy numbers to reduce deletion phenotypes.

The exemplary layout of FIG. 5B demonstrates that new stage 1 and stage 2 vectors can also be engineered depending on the needs of the user (e.g., high copy or low copy number, or different antibiotic resistance marker).

It is noted that the efficiency of digestion and ligation of PUCT transcription units may change as a function of number of PUCT units ligated together, length of PUCT units, and secondary structure of PUCT units. Therefore, in some embodiments, the assembly strategy may be designed to compensate for, e.g., a decrease in efficiency of ligation by, e.g., increasing digestion and ligation cycles, selecting for smaller colonies after transformation, and/or utilizing lower-copy final vectors to reduce expression load.

Figure 5C:
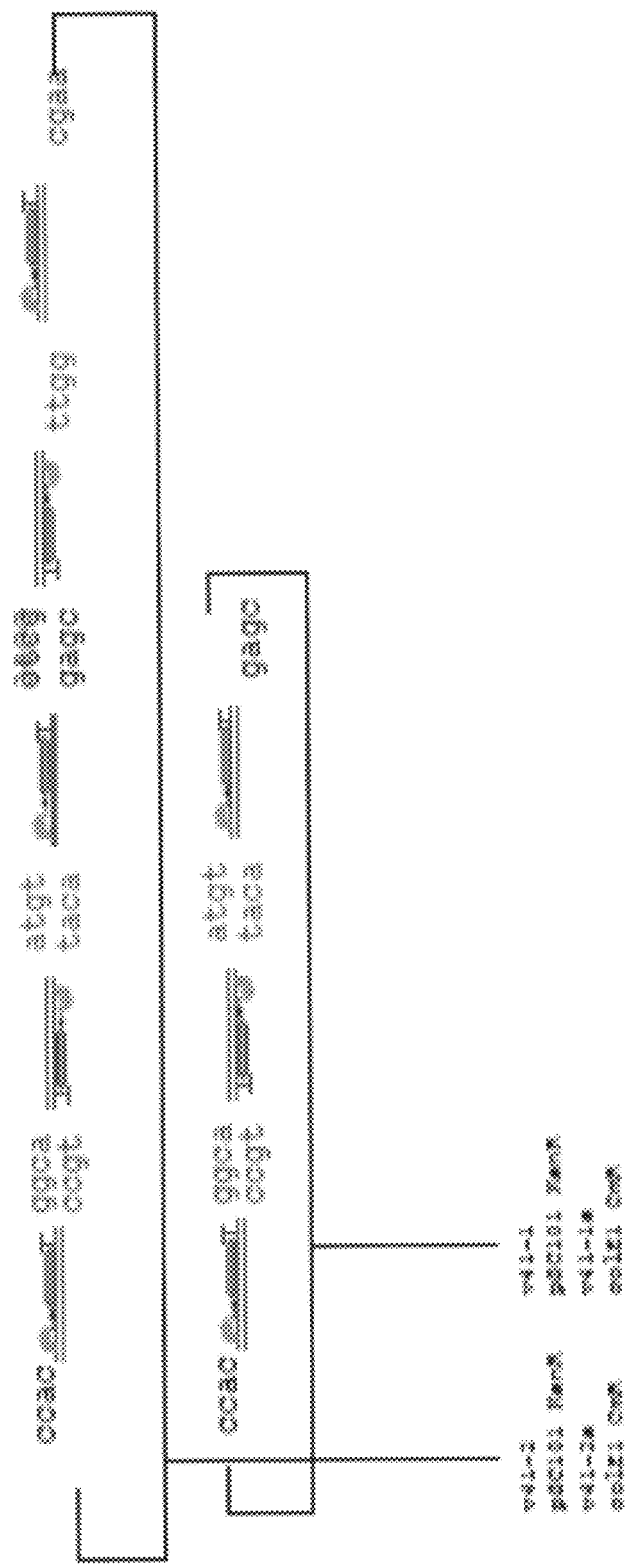
FIG. 5C illustrates an exemplary assembly strategy of 5 transcription units into 1 vector (top) and 3 to 1 (bottom) with new vectors that use different cohesive ends.

If 6 transcription units are not available at the same time, one can easily scale down by changing the end sticky end on the stage 2 vector. Shown in FIG. 5C is an example using 5 PUCT transcription units and an example using 3 PUCT expressible units. One can also replace PUCT expressible units with randomly generated DNA to act as filler.

To demonstrate the power of the assembly method disclosed herein, one of ordinary skill in the art will appreciate that by using, e.g., FIG. 5B's assembly method, if 18 PUCT transcription units were made, within two stages this assembly method would allow for 3 in vivo compatible plasmids using only two cycles of cloning. This could take only 1 week or less (as opposed to the current standard of multiple months in conventional cloning), and would be sufficient to express the largest known synthetic circuits in *E. coli* (Moon, Lou, Tamsir, Stanton, & Voigt, 2012). In addition, the assembly needs only minimal planning before implementation and does not require re-engineering of vectors after cloning. By dramatically reducing the number of cloning cycles, this procedure saves significant time and requires less user know-how in order to assemble complete circuits. It also allows for the testing of intermediate plasmids in an alternative system, such as an in vitro cell-free transcription-translation system.

It should also be noted that the present technology is different than the GoldenBraid assembly disclosed by Sarrion-Perdigones et al. (2011) PLoS ONE 6(7): e21622, doi:10.1371/journal.pone.0021622, incorporated herein by reference. GoldenBraid by design only permits binary assembly, i.e., joining of two modules, using an automated process. Thus, for 8 transcription units it takes 3 cycles to get into 1 plasmid using GoldenBraid. In contrast, the present technology significantly limits the number of cycles needed (e.g., only 1 or 2 cycles needed) by allowing more than 2 modules to be assembled into one module. While less of an "automated" process compared to GoldenBraid and requiring more advanced planning, the present technology achieves significant time and labor savings. For example, the efficient ligation of 6 large PUCT units (each of ~1-2 kb) and a vector (~2-3 kb) into one unit (~8-15 kb) is demonstrated in the present technology.

The method outlined herein is additionally different from GoldenBraid by providing flexibility in choosing intermediate vectors to be compatible for end-test conditions, such that modules of the circuit can be tested independently or in combination in vitro in vivo without interrupting the complete circuit assembly process. The in vitro testing is significant, as the GoldenBraid technology is optimized entirely for in vivo expression of the final assembly (which takes significant time to complete). Therefore, the present technology allows for testing and re-engineering of the circuit during the engineering process, instead of requiring the entire circuit be completed before implementation.

The present technology can be used in connection with the "design, build, test" (DBT) cycle for prototyping and debugging a biomolecular circuit as disclosed in U.S. patent application Ser. No. 15/046,374 filed Feb. 17, 2016, entitled "CELL-FREE BIOMOLECULAR BREADBOARDS AND RELATED METHODS AND ARRANGEMENTS", the disclosure of which is incorporated herein by reference. For example, following rational design and model of a circuit or pathway comprising a plurality of parts, the individual parts can be built and combined to form the designed circuit or subcircuits for in vitro testing as follows:

A specific concentration of each part is mixed in a container containing extract and buffer, such as the TX-TL system disclosed herein. Different concentrations of different parts can be used to create a collection of variants that will be tested.

Additional chemicals can be added to the container to establish different conditions under which the part is to be characterized. For example, inducers may be added in different concentrations to characterize the function of a repressor protein.

The container is heated to a temperature an incubated for a period of time.

A measurement is taken, using an optical assay (absorbance or fluorescence), a chemical assay (mass spec) or other analytical technique.

The previous two steps are iterated at a specific rate and for a duration of time.

Optionally, to build confidence in the in vitro results, an in silico approach can also be used that uses as an input characterized parts and simulates, in silico, different formulations of the parts to form the design circuit or subcircuits. This is done most accurately to reflect the findings one would obtain in vitro; however, the in silico toolbox can also provide data on the predicted function of the circuit in vivo.

Using the measurement data from in vitro testing, the performance of the circuit can be characterized by analyzing the data and determining which combinations of parts, and in what relative concentrations, when combined together implement the function that was designed originally. At the end of this step, a single DBT cycle is complete. At this stage, if the circuit does not perform as designed, the data from this step and previous steps can be used to redesign the circuit, returning to any prior step in the workflow.

Once a specific combination of parts has been determined to provide the designed function in the breadboard, the parts can be combined so that multiple parts are assembled on pieces of DNA compatible with the cell using the present technology. Often this DNA is a circularized molecule referred to as a plasmid. Typically, the circuit is consolidated onto 1, 2 or 3 plasmids that have compatible origins of replications (e.g., can survive in the cell together). In this form, the circuit can be tested both in vitro (using the cell-free system) and in vivo (using a cell).

The following steps can be used to create the plasmid form of the circuit that will be verified:

The specific parts can be designed to be in the stoichiometric ratios determined to be the most effective in vitro to match in vivo. E.g., items that require low expression are put on low copy number plasmids whereas those that require high expression which are put on high copy number plasmids. Promoter or ribosome binding site (RBS) can also be varied in strengths to modulate expression level.

The individual parts are then engineered to form stage 1 constructs, using Golden Gate Assembly or any other suitable assembly methods.

All parts for a designed circuit can then be engineered to form stage 2 constructs (e.g., on 1-3 plasmids) such that the final plasmids can be directly transformed into a cell for verification, without the need for further cloning.

In vitro verification can include the following steps:

A specific concentration of the plasmid or other DNA sequence that contains multiple parts is mixed in a container containing extract and buffer such as the TX-TL system disclosed herein. If more than one piece of DNA is used, different concentrations of different plasmids can be used to create a collection of variants that will be tested.

Additional chemicals can be added to the container to establish different conditions under which the part is to be characterized. For example, inducers may be added in different concentrations to characterize the function of a repressor protein.

The container is heated to a temperature an incubated for a period of time.

A measurement is taken, using an optical assay (absorbance or fluorescence), a chemical assay (mass spec) or other analytical technique.

The previous two steps are iterated at a specific rate and for a duration of time.

The output from the in vitro verification step can be a set of data that measure the performance of the circuit under desired conditions in a cell-free environment. These data are compared to the desired operation of the circuit (as represented by the initial design and model step). If the results are the same, the circuit is operational in an in vitro environment. Depending on the application, this in vitro version of the circuit can be used directly in applications. If the output from this step does not match the model, the data from the in vitro verification step and previous steps can be used to redesign the circuit, returning to any prior step in the workflow.

In vivo verification can include the following steps:

Cells are chemically, electrically or thermally treated to allow them to transport DNA from their external environment into the cytoplasm of the cell.

Plasmids containing the DNA implementing a circuit, instantiated on one or more (e.g., 1-3) plasmids, are introduced into the environment of the treated cells.

The plasmids are transformed into the cells by the introduction of an environmental stimulus (e.g., temperature) that causes at least a fraction of the cells to incorporate one or more plasmids into the cytoplasm.

The cells are transferred to container that contains growth media and a selecting agent (e.g., an antibiotic), such that only those cells containing the desired circuit elements can divide and grow.

The container is heated to a temperature and incubated for a period of time.

A measurement is taken, using an optical assay (absorbance or fluorescence), a chemical assay (mass spec) or other analytical technique.

The previous two steps are iterated at a specific rate and for a duration of time.

The output from the in vivo verification step can be a set of data that measure the performance of the circuit under desired conditions in a cell. These data are compared to the desired operation of the circuit (as represented by the design and model step). If the results are the same, the circuit is operational in an in vivo environment.

EXAMPLES

Example 1: Assembly of a Nested Feed-Forward Loop

FIGS. 6A-6C illustrates the cloning of two variants of a 6-piece nested feed-forward loop. In FIG. 6A, a promoter, UTR (and/or) coding sequence, and terminator are first incorporated into a "PUCT" transcription construct over 6 different plasmids (stage 1 constructs). For example for construct 362p, a "P" unit, "UC" unit, and "T" unit are cloned into vector 10-2 in a one-pot reaction by digestion with BsaI. Then, still referring to FIG. 6A, the 6 constructs on 6 different plasmids are consolidated onto two different plasmids (stage 2 constructs 411 in v2-3 and 412 in v2-4), where the digestion of v10-2, v10-3b, and v1-1 with BbsI allow cloning into v2-3 or v-2-4 in a one-pot reaction. For example, constructs 362p, 363p, 287p and v2-3 are combined together to assemble plasmid 411 in v2-3. Stage 2 constructs 411 in v2-3 and 412 in v2-4 can be directly tested in vivo with, e.g., IPTG induction in JW0336 cells.

FIG. 6B shows the same procedure for different variants of the nested feed-forward loop, from 6 different stage 1 constructs to 2 stage 2 constructs, 413p in v2-3 and 414p in v2-4.

In the final stage shown in FIG. 6C, 411p in v2-3 and 412p in v2-4 are combined together with vector v1-4 and BsaI in a one-pot reaction to produce 415p v1-4, which contains the 6-transcription unit circuit. 413p in v2-3 and 414p in v2-4 are combined to produce 416p v1-4. Final constructs 415p v1-4 and 416p v1-4 can be tested directly in vivo with IPTG/aTc/3OC6/3OC12 in JW0336 cells.

It is worth noting that the vectors are designed beforehand to facilitate compatibility. In addition, all constructs in the same vectors are interchangeable. For example, 362p, 364p, 334p, or 367p are all in v10-2 and can be used interchangeably.

In specific, in FIG. 6A 362p contains a small trigger RNA from Green et al. (Cell 2014 Nov. 6; 159(4):925-39) that is controlled by a strong lambda-phage (POr21Pr) constitutive promoter, repressible in the presence of a lambda-phage repressor (lambda-CI). 363p has a constitutive promoter, J23150, in front of a lacI repressor, that is normally "off" but can be activated by expression of the trigger1 RNA from 362p. 287p has a lac promoter (that can be repressed by lacI repressor) that encodes for a sfGFP (reporter) tagged with an ssrA degradation tag, that is normally "off" but can be activated by expression of the trigger1 RNA from 362p. This module is independent, i.e., the three plasmids are functional by themselves. This module produces a pulse in vivo, e.g., an increase in signal by reporting from the sfGFP in 287p, followed by a decrease in signal as lacI is produced from 363p to shut off expression of 287p. sfGFP is then degraded by ClpXP AAA+ proteases or and/or diluted from cellular growth and division.

Because the module is independent, 362p, 363p, and 287p are purposely chosen to be on compatible vectors (cmR p15A, kanR pSC101, ampR colE1) such that they can be co-transformed in vivo for testing, while still able to be directly used in the second assembly reaction.

A separate module, on the bottom of FIG. 6A, is composed of 334p, 368p and 369p. 334p has a lac promoter (that can be repressed by lad repressor) that encodes for a lasR that is normally "off" but can be activated by expression of the trigger1 RNA from 362p. 368p has a las promoter (that can be activated by lasR from 334p) in front of a tetR coding sequence. 369p has a las promoter with a built in tetO1 operator, that can be repressed by tetR produced by 368p, and expresses mRFP with an ssrA degradation tag. This module, when activated by the top module, also produces a pulse in vivo of mRFP. It is nested, as the second feed-forward loop (334p, 368p, 369p) requires activation from the first feed-forward loop (362p, 363p, 287p).

362p in FIG. 6A is assembled by the following protocol: v10-2 (2217 bp 241 ngul 66 ng): 0.28 uL, P52 Or2-Or1-Pr1-short, short attachment (90 bp 53 ngul 2 ng): 0.51 uL at 1:10 dil, UC10 green_trigger1_1stgen_17 bp (AGCA) (98 bp 222 ngul 2 ng): 1.33 uL at 1:100 dil, T17 T500_noGap, short attachment, (AGCA) (70 bp 204 ngul 2 ng): 1.03 uL at 1:100 dil, BSA at 10x: 1.00 uL, T4 ligase Buffer: 1.00 uL, BsaI/HF: 0.67 uL, T4 Ligase 2 mil units: 0.67 uL, ddH20: 3.52 uL. Assembly conditions were: 3 min at 37° C., 4 min at 16° C., cycled 25 times; followed by 5 min at 50° C., 5 min at 80° C.

1 uL of the assembly reaction for 362p is then transformed into a JM109 competent sub-cloning strain following a published protocol from Zymo Mix-and-Go JM109 chemical transformation. After transformation, cells are recovered for 1 hour at 37° C. in SOC media, and then plated on chloramphenicol-resistant LB plates for overnight growth. This strain is chosen, because although expression is driven by a strong POr21Pr promoter, the trigger RNA itself is non-toxic. If the expressible unit is toxic, then an alternate strain can be chosen (e.g., a KL740 strain from the Yale E. coli genetic stock center) to repress expression.

Figure 7A:
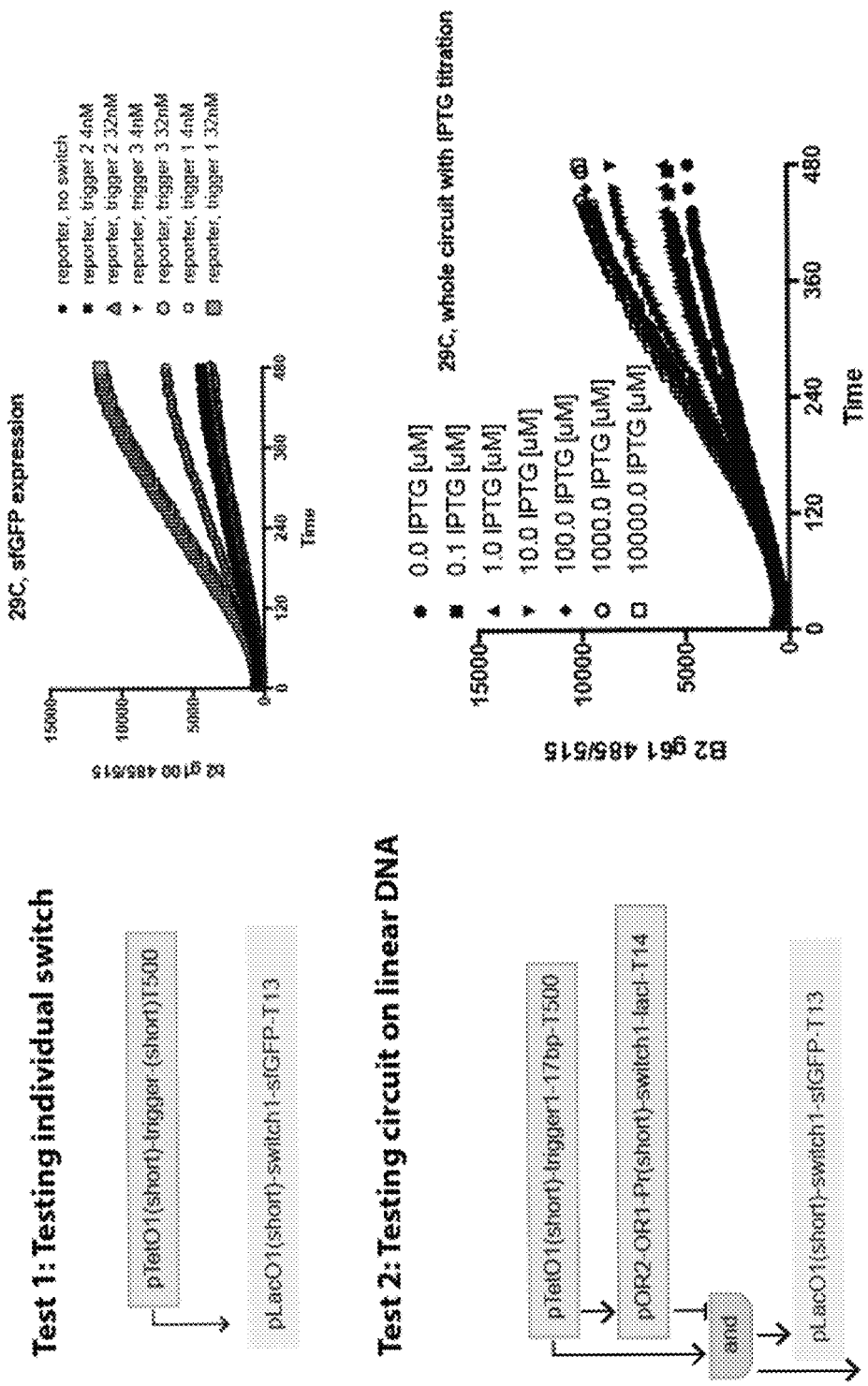
FIG. 7A illustrates the testing of an exemplary circuit assembled using the present technology, a feed-forward loop and nested forward-loop, in vitro in a cell-free transcription-translation system to determine circuit performance.

In lieu, 362p and other DNAs can also be amplified by PCR and tested immediately in vitro in linear form, or can be transformed, miniprepped, and tested in vitro or in vivo in plasmid form. FIG. 7A shows representative data that would be collected by testing rapid assembly linear DNA pieces from this module in vitro. In FIG. 7A, top, is a demonstration that a specific trigger (trigger 1) can activate a specific switch (switch 1) in vitro in a dose-dependent manner. In FIG. 7A, bottom, is a demonstration that linear DNA can be used to implement the whole circuit in vitro. The circuit responds to increased IPTG by increasing signal production as lad repression is lifted.

Figure 7B:
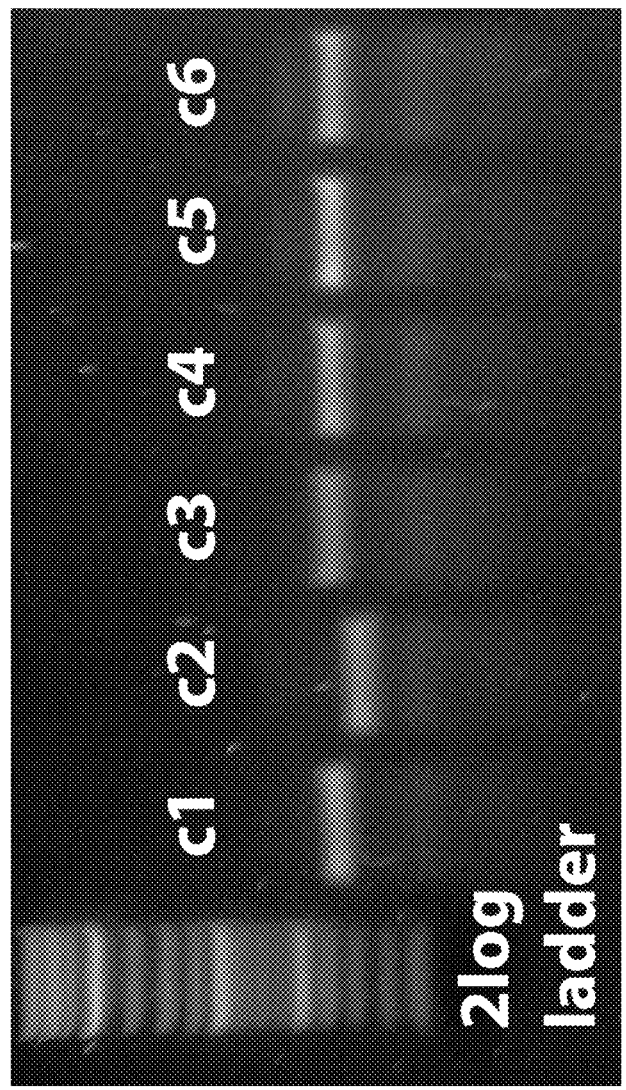
FIG. 7B illustrates the screening of an exemplary plasmid containing one transcription unit (in a stage 1 construct), by colony PCR, to determine plasmids for sequencing (not shown).

Resulting individual colonies undergo colony PCR using primers binding to the v10-2 vector (TTCTCATGTTT-GACAGCTTATCA (SEQ ID NO.: 14), ATAACT-CAAAAAATACGCCCG (SEQ ID NO.: 15)) that are expected to produce a 354 bp construct. As demonstrated in FIG. 7B, c1 and c3-c6 produce correct sized bands against a 2 log ladder (NEB N3200), while c2 is an incorrect band and likely ligation of an empty vector. The successful production of 362p is confirmed by Sanger Sequencing (not shown).

Each of 363p, 287p, 364p, 365p, 367p, 368p, 369p is prepared similarly as 362p using the same procedure, but varying the individual P, U, (UC), C, or T pieces and resistance of selection.

362p, 363p, and 287p can then be assembled into 411p in FIG. 6A by the following protocol: v2-3: 2568 bp/203 ngul at 35.1 ng→0.17 uL; 362p: 32.3 ng, 2363 bp, 40 ngul→0.81 uL; 363p: 66 ng, 4833 bp, 33 ngul→2 uL; 287p: 45.8 ng, 3352 bp, 482 ngul→1 uL of 1:10 dil, BSA at 10x-1 uL, T4 Ligase-1 uL, BbsI-0.66 uL, T4 Ligase 2 mil-0.66 uL, water-2.7 uL. Assembly conditions were: 3 min at 37° C., 4 min at 16° C., cycled 25 times; followed by 5 min at 50° C., 5 min at 80° C. 411p is then transformed into a JM109 strain, plated on spectinomycin-resistant LB plates, grown, screened by colony PCR, and sequenced as done for 362p.

We note that 411p assembles 362p, 363p, and 287p in a stage 2 vector v2-3 that is specR p15A. This is chosen purposely, as specR does not share the resistance marker of 362p, 363p, or 287p (to avoid background selection from transformed original plasmids during the selection). In addition, cmR and p15A allow this plasmid to be tested in vivo with another plasmid, 361p, which produces additional trigger RNA and is ampR, colE1.

412p is prepared similarly as 411p but using 334p, 368p, 369p, and v2-4.

415p in FIG. 6C is the final testing plasmid and can be assembled by the following protocol: 411p: 5020 bp, 68 ngul, 62 ng→0.91 uL, 412p: 5312 bp, 79 ngul, 66 ng→0.84 uL, v1-4, 2217 bp, 267 ngul, 28 ng→1.05 uL 1:10 dil, Bsa-10x→1 uL, T4L Buffer→1 uL, BsaI-HF→0.66 uL, T4L→0.66 uL, H20→3.88 uL. Assembly conditions were: 3 min at 37° C., 4 min at 16° C., cycled 25 times; followed by 5 min at 50° C., 5 min at 80° C. 415p is then transformed into a JM109 strain, plated on chloramphenicol-resistant LB plates, grown, screened, and sequenced.

Figure 7C:
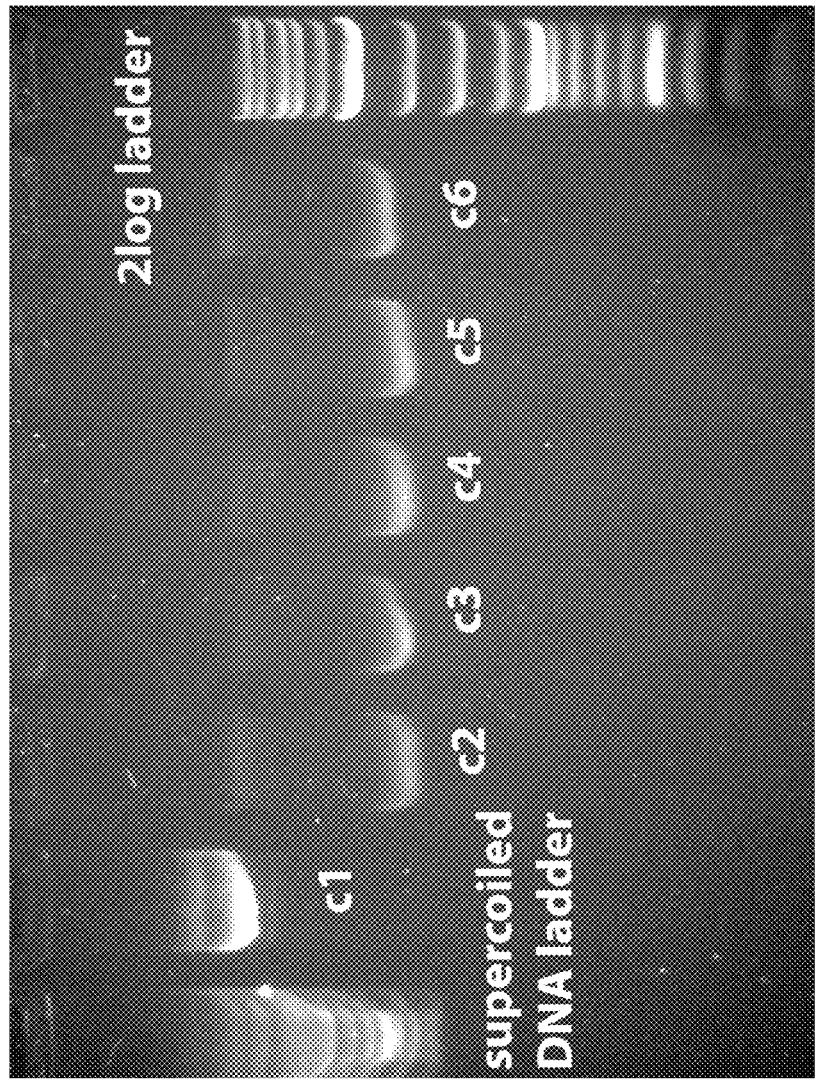
FIG. 7C illustrates, in one embodiment, the screening of 6 variants of a final plasmid assembled using the present technology, containing 6 transcription units (from 6 stage 1 constructs, into a stage 2 construct) by plasmid size on a gel, with one plasmid (c1) out of 6 correctly sized.

Note that for larger plasmids such as 415p (7,461 bp) and 416p (8,308p), a significant metabolic load may be introduced into the cell that will slow growth. In addition, the efficiency of ligation may be reduced. Therefore, it may be necessary to choose smaller or slower-growing colonies, and to screen additional constructs. In this example, for 416p colonies were grown and miniprepped to determine size rather than by colony PCR. The resulting plasmids (416p clones c1 to c6) are shown in FIG. 7C, compared to a supercoiled DNA ladder (NEB N0472) and 2 log ladder (NEB N3200). In this example, only 416p-c1 is of the correct size.

415p and 416p are considered the final circuit (with 415p combining 6 PUCT transcriptional units and 416p combining 6 PUCT transcriptional units) and can be used for testing in vivo in a final testing strain, such as JW0336 (Yale E. coli genetic stock center).

It should be noted that while in this example, the first feed-forward loop (362p, 363p, 287p) and the second feed-forward loop (334p, 368p, 369p) are assembled in a 2-step process into one plasmid, one skilled in the art would appreciate that all 6 transcription units can be assembled together in a 1-step assembly using the present technology.

Example 2: Assembly of an Oscillator Plasmid

Figure 8A:
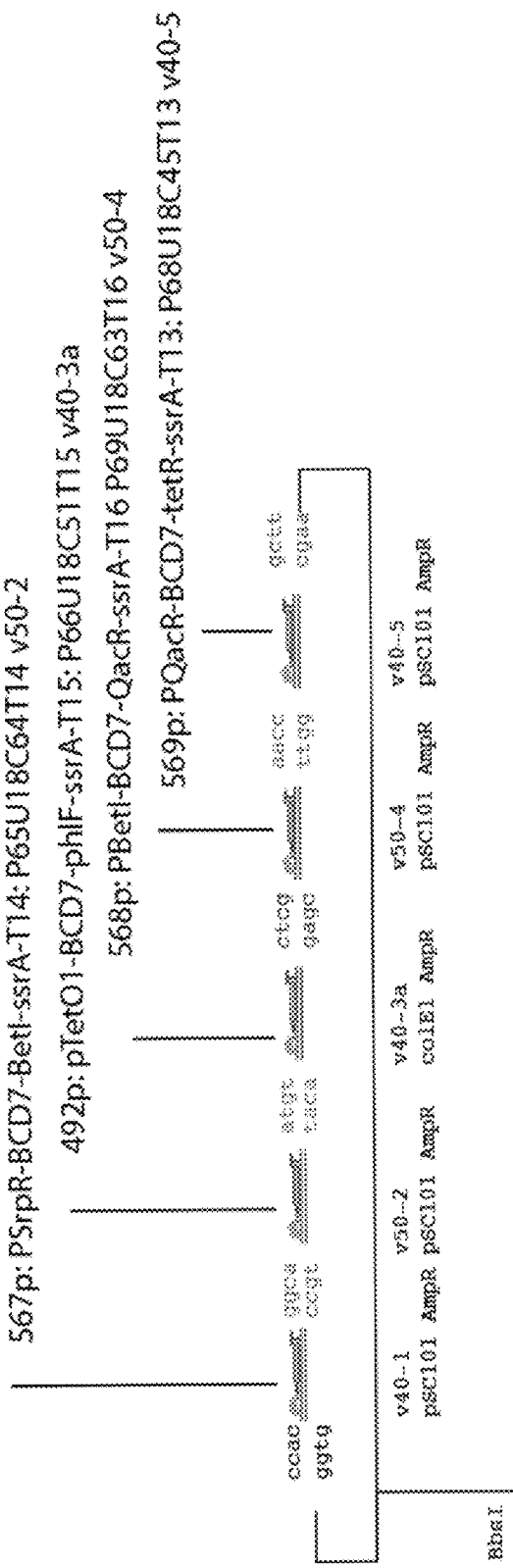
FIGS. 8A-8C illustrate, in one embodiment, assembly and testing of a variant of a 5-node oscillator. Specifically.

FIG. 8A illustrates the assembly of a 5 PUCT transcriptional unit oscillator plasmid into a final stage 2 vector, v41-2. In FIG. 8A (top), 5 individual PUCT transcriptional units (490p, 567p, 492p, 568p, and 569p) are assembled into compatible stage 1 constructs (v40-1, v50-2, v40-3a, v50-4, v40-5, respectively). These 5 plasmids can then be assembled with a v41-2 vector in a one-pot reaction with BbsI Type IIs restriction enzyme to generate the final 5n2 plasmid.

Figure 8B:
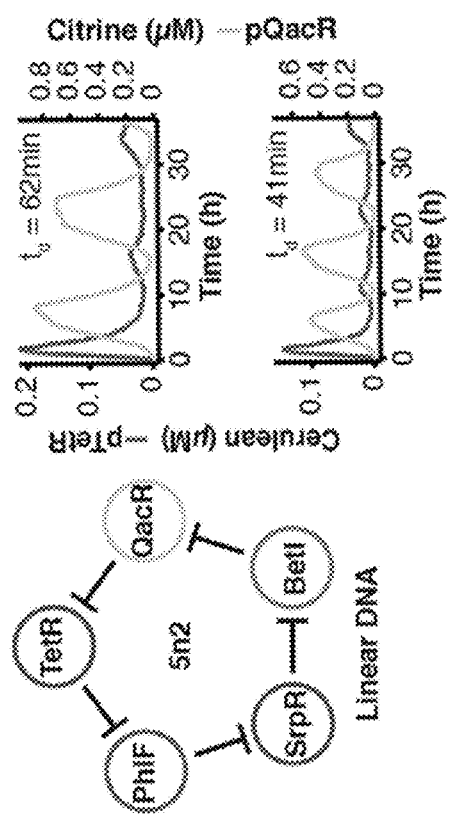
Figure 8C:
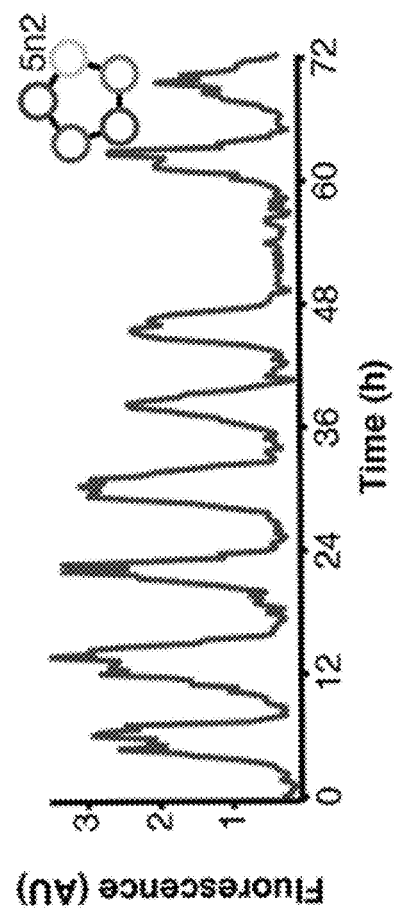

490p is a SrpR-ssrA repressor protein driven by a PhlF promoter. SrpR-ssrA represses the promoter on 567p, which is a BetI-ssrA repressor driven by a SrpR promoter. BetI-ssrA represses the promoter on 568p, which is a QacR-ssrA repressor driven by a BetI promoter. QacR-ssrA represses the promoter on 569p, which is a TetR-ssrA repressor driven by a QacR promoter. TetR prepresses the promoter on 492p, which is a PhlF-ssrA repressor driven by a TetR promoter. PhlF represses 490p. This ring of repression produces in an in vitro transcription-translation system an oscillating waveform over time, when the output is read on any axis (e.g. pTetR-Cerulean, pQacR-Citrine) (FIG. 8B). Note that this in vitro expression is done with 5 strands of linear DNA and 2 reporter plasmids; the linear DNA can be produced immediately from the assembly procedure described in this technology. The 5 plasmids (490p, 567p, 492p, 568p, and 569p), when combined into one plasmid (5n2) and transformed into a JS006 strain (Nature. 2008 Nov. 27; 456(7221):516-9) with a reporter plasmid such as pPhlF-BCD22-sfGFP-ssrA (LAA) (ampR, colE1), produce a corresponding waveform in vivo over time (FIG. 8C).

As an exemplary stage 1 plasmid, 567p, P65U18C64T14 v50-2, is assembled by combining: v50-2 (3647 bp 47 ngul 66 ng): 1.42 uL, P65 pSrpR, Stanton_14 (115 bp 16 ngul 2 ng): 1.31 uL at 1:10 dil, U18 BCD7(AATG) (141 bp 68 ngul 2 ng): 0.38 uL at 1:10 dil, C64 betI-ssrA (AATG), orig. E. coli (650 bp 40 ngul 11 ng): 2.97 uL at 1:10 dil, T14 ECK120033736 (164.6x), short attachment (95 bp 187 ngul 1 ng): 0.93 uL at 1:100 dil, BSA at 10x: 1.00 uL, T4ligase Buffer: 1.00 uL, BsaI/HF: 0.67 uL, T4Ligase 2 mil units: 0.67 uL. Assembly conditions were: 3 min at 37° C., 4 min at 16° C., cycled 25 times; followed by 5 min at 50° C., 5 min at 80° C.

1 uL of the assembly reaction for 567p is then transformed into a JM109 competent sub-cloning strain following a published protocol from Zymo Mix-and-Go JM109 chemical transformation. After transformation, cells were plated on carbenicillin-resistant LB plates for overnight growth. Colonies can then be isolated for sequencing and verification.

Note that 490p, 567p, 568p, and 569p are purposely chosen to be transformed into a pSC101 AmpR backbone, as each of these promoters (pPhlF, pSrpR, pBetI, and pQacR, respectively) do not have easily accessible strains that have repressors to repress expression. Therefore, a low-copy pSC101 vector is preferable to avoid toxicity. However, 492p is under control of a pTetR promoter, which can be repressed by tetR overexpressing strains such as MG1655Z1. Therefore, if using the MG1655Z1 strain, a high-copy colE1 vector can be used.

In lieu, each post-assembled, pre-transformed plasmid and other DNAs can also be amplified by PCR and tested immediately in vitro in linear form, or can be transformed, miniprepped, and tested in vitro or in vivo in plasmid form. FIG. 8B is a demonstration of a circuit run off of comparably produced linear DNA.

To make the stage 2 plasmid 5n2, assembled are: V41-2: 3581 bp, 64 ngul, 52 ng→0.81 uL, 567: 30 ngul, 4483 bp, 65 ng→2.17 uL, 568: 34 ngul, 4450 bp, 65 ng→1.91 uL, 569: 66 ngul, 4555 bp, 66 ng→1 uL, 490 old: 4555 bp, 172 ngul, 66 ng→0.38 uL, 492: 3204 bp, 501 ngul, 46 ng→0.28 uL 1:3 dil, Bsa10x: 1 uL, T4L: 1 uL, BbsI: 0.66 uL, T4Ligase: 0.66 uL, H2o: 0.13 uL. Assembly conditions were: 3 min at 37° C., 4 min at 16° C., cycled 25 times; followed by 5 min at 50° C., 5 min at 80° C. 5n2 is then transformed into a JM109 strain, plated on kanamycin-resistant LB plates, grown, screened, and sequenced.

5n2 is a very large plasmid (8014 bp) using 5 active PUCT transcriptional units; therefore a significant metabolic load may be introduced into the cell that will slow growth. In addition, the efficiency of ligation may be reduced. Therefore, it may be desirable to choose smaller or slower-growing colonies, and to screen additional constructs.

Materials and Methods

Cell-free expression preparation and execution: Preparation of the cell-free TX-TL expression system was done according to previously described protocols, resulting in extract with conditions: 8.9-9.9 mg/mL protein, 4.5-10.5 mM Mg-glutamate, 40-160 mM K-glutamate, 0.33-3.33 mM DTT, 1.5 mM each amino acid except leucine, 1.25 mM leucine, 50 mM HEPES, 1.5 mM ATP and GTP, 0.9 mM CTP and UTP, 0.2 mg/mL tRNA, 0.26 mM CoA, 0.33 mM NAD, 0.75 mM cAMP, 0.068 mM folinic acid, 1 mM spermidine, 30 mM 3-PGA, 2% PEG-8000.14 Unless otherwise specified, one extract set "e10" was used consistently throughout the experiments to prevent variation from batch to batch and to test feed-forward loop circuits in vitro. Extract "eZS4" was similarly prepared for oscillator in vitro work. Extract "eZS4" was prepared using above conditions but using a JS006 starting strain. TX-TL reactions were conducted in a volume of 10 µL in a 384-well plate (Nunc) at 29° C., using a three tube system: extract, buffer, and DNA. When possible, inducers such as IPTG or purified proteins such as gamS were added to a mix of extract and buffer to ensure uniform distribution. When using a plate reader, for deGFP, samples were read in a Synergy H1 plate reader (Biotek) using settings for excitation/emission: 485 nm/525 nm, gain 61. For mRFP, settings were 580 nm/610 nm, gain 61 or 100. All samples were read in the same plate reader, and for deGFP and mRFP rfu units were converted to µM of protein using a purified deGFP-His6 standard and purified mRFP standard. Unless otherwise stated, end point measurements are after 8 h of expression at 29° C.

Cell-free in vitro execution of feed-forward loop: Cell-free experiments testing individual switches were run with 8 nM of a rapid assembly linear DNA product of pLac-switch (from Green et al. 2014)-sfGFP-ssrA-ECK120029600 and 4 nM-32 nM of rapid assembly linear DNA products pTet-trigger-T500, where three separate triggers are tested and one is known to activate the switch tested in vivo. Reactions are also run with gamS at 3.5 uM, and IPTG of 1 mM. Cell-free experiments testing whole circuits were run with 32 nM of a rapid assembly linear DNA product of pTet-trigger-T500, 8 nM of a rapid assembly linear DNA product of pLac-switch-sfGFP-ssrA-ECK120029600, and 4 nM of a rapid assembly linear DNA product of pOR21Pr-switch-lacI-ECK120033736. Reactions are also run with gamS at 3.5 uM, and varying concentrations of IPTG.

GamS Protein Purification: The composition of buffers used was as follows: buffer L, 50 mM Tris-Cl pH 8, 500 mM NaCl, 5 mM imidazole, 0.1% Triton X; buffer W, 50 mM Tris-Cl pH 8, 500 mM NaCl, 25 mM imidazole; buffer E, 50 mM Tris-Cl pH 8, 500 mM NaCl, 250 mM imidazole; buffer S, 50 mM Tris-Cl pH 7.5, 100 mM NaCl, 1 mM DTT, 1 mM EDTA, 2% DMSO. A frozen stock of P_araBAD-gamS in a BL21-DE3 E. coli strain was grown overnight in LB-carbenicillin media. 100 mL was used to inoculate 1 L LB-carbenicillin to an OD 600 nm of 0.4-0.6 at 37° C., 220 rpm. Cells were then incubated to 0.25% arabinose (final concentration) and grown for four additional hours at 25 C, 220 rpm, before being pelleted and frozen at −80° C. Cells were resuspended in buffer L, mechanically lysed and incubated with Ni-NTA agarose (Qiagen). Ni-NTA agarose was washed twice with 15 column volumes of buffer W and eluted in buffer E. Fractions with a ~13 kD band were concentrated and dialyzed into buffer S overnight and further purified on a 26/60 Sephadex 75 column. Protein concentration was verified by Bradford, concentrated to 3 mg/mL using an Ultra-0.5 3K MWCO Centrifugal Filter (Ambion), and stored in buffer S at −80° C. Protein purity was verified by gel. Purification steps were verified by SDS-PAGE gel electrophoresis.

Plasmid DNA and PCR Product Preparation: Plasmids used in this study were constructed using standard cloning procedures and maintained in a KL740 strain if using an OR2-OR1 promoter (29° C.), a MG1655Z1 strain if using a Pl-tetO1 or Pl-lacO1 promoter, a BL21-DE3 strain for protein purification, a BL21 strain for promoter characterization, or a JM109 strain for all other constructs. KL740 upregulates a temperature sensitive lambda cI repressor, and MG1655Z1 upregulates tetR and laI. PCR products were amplified using Pfu Phusion Polymerase (New England Biolabs) for all constructs, and were DpnI digested. Plasmids were either miniprepped using a PureYield column (Promega) or midiprepped using a NucleoBond Xtra Midi column (Macherey-Nagel). All plasmids were processed at stationery phase. Before use in the cell-free reaction, both plasmids and PCR products underwent an additional PCR purification step using a QiaQuick column (Qiagen), which removed excess salt detrimental to TX-TL, and were eluted and stored in 10 mM Tris-Cl solution, pH 8.5 at 4° C. for short-term storage and −20° C. for long-term storage.

In vitro Linear DNA Assembly. Linear DNA fragments were amplified using Pfu Phusion Polymerase (New England Biolabs), DpnI digested for 5 min at 37° C. (New England Biolabs) while verified with agarose gel electrophoresis, and PCR purified using previously described procedures. Fragments were then assembled in vitro using either isothermal assembly or Golden Gate assembly. For isothermal assembly, Gibson Assembly Master Mix (New England Biolabs) was used according to manufacturer instructions with 1:3 molar ratio vector/insert, and reacted at 1 h at 50° C. For Golden Gate assembly, a 15 μL reaction was set up consisting of equimolar amounts of vector and insert, 1.5 μL 10×NEB T4 Buffer (New England Biolabs), 1.5 μL 10×BSA (New England Biolabs), 1 μL BsaI (New England Biolabs), and 1 μL T4 Ligase at 2 million units/mL (New England Biolabs). Reactions were run in a thermocycler at either 10 cycles of 2 min/37° C., 3 min/20° C., 1 cycle 5 min/50° C., 5 min/80° C. or 25 cycles of 3 min/37° C., 4 min/16° C., 1 cycle 5 min/50° C., 5 min/80° C. For Golden Gate assembly, constructs with internal BsaI or BbsI cut sites were silently mutated beforehand using a QuikChange Lightning Multi Site-Directed Mutagenesis kit (Agilent).

Rapid Assembly Product Protocol. The in vitro linear DNA assembly protocol was followed. Overlap primers were then designed to bind over the vector:promoter and vector/terminator junctions such that the Tm of binding on each junction side was below 40° C. Then, 1 μL of the resulting assembly product was PCR amplified for 35 cycles in a 50 μL PCR reaction, and verified by agarose gel electrophoresis. If the resulting band was 80% or more pure, the DNA was PCR purified using previously described procedures and used directly in TX-TL.

Protein purification: For fluorescent proteins eGFP, mRFP, and Venus and variants eGFP-ssrA, mRFP-ssrA, and Venus-ssrA, coding sequences were cloned into a T7-lacO inducible vector containing a N-terminus His6 tag using standard techniques and propagated in a BL21-DE3 strain (New England Biolabs). Proteins were purified following a similar protocol as in Hodgman et al., Metab Eng, 2012. 14(3): p. 261-9, but were grown in TB broth in lieu of LB broth, induced with 1 mM IPTG (final concentration), and selected for a band between 25 kDa-35 kDa corresponding to the fluorescent protein in question. Fluorescent proteins were further processed in a Supradex 20 10/300 column to select for pure, active proportions, and flash-frozen at −80° C. in a storage buffer consisting of: 50 mM Tris-Cl pH 7.5, 100 mM NaCl, 1 mM DTT, 1 mM EDTA, 2% DMSO. Final concentrations were: deGFP-ssrA, 164.8 uM; deGFP, 184.8 uM; mRFP-ssrA, 185.6 uM; mRFP, 170.6 uM; Venus-ssrA, 87.9 uM; Venus, 147.5 uM.

In vivo strain preparation and testing for feed-forward loops. For in vivo assays, plasmids were cloned into compatible vectors and chemically transformed into a compatible strain, such as JW0336. For single strain assays, cells were selected for on antibiotic resistant agar plates before use. For multi-panel assays, cells were recovered for 2 hours at 29 C. in SOC medium (Sigma) before outgrowth at a 1.25% dilution in MOPS-EZ Rich (Teknova) 0.4% glycerol selective media containing 10 μg/mL chloramphenicol, 50 μg/mL kanamycin, 100 μg/mL carbenicillin, 100 μg/mL spectinomycin, or equivalent antibiotic dependent on strain and plasmid and storage at −80 C. To conduct the in vivo assays, cells were grown in the same selective MOPS media to stationery phase at 29° C. Cells were then diluted 1% into 500 uL per well in 96-well MatriPlates (Brooks Life Sciences) with half-antibiotic concentration previously used. Three plate readers were used (Biotek H1/MF), which were calibrated for fluorescent intensity and absorbance. Plates were measured every 6 minutes at deGFP, 485 nm/515 nm gain 61 and 100, and OD, 600 nm under a linear continuous shaking mode. At OD 0.1-0.2, cells were induced with appropriate small molecule (such as aTc, IPTG, or 3OC12HSL) and then measured for an additional 16 hours until stationery phase.

Steady-state cell-free in vitro testing for oscillators: Experiments were performed in a microfluidic nano-reactor device as described in Niederholtmeyer et al., PNAS 2013 vol. 110 no. 40 15985-15990, with some modifications to optimize the conditions for the lysate-based TX-TL mix. Reaction temperature was 33° C. Lysate was diluted to 2× of the final concentration in 5 mM HEPES 5 mM NaCl buffer (pH 7.2). The reaction buffer mix was combined with template DNA and brought to a final concentration of 2×. For a 24 h experiment 30 μl of these stocks were prepared. During the experiment, lysate and buffer/DNA solutions were kept in separate tubing feeding onto the chip, cooled to approximately 6° C., and combined on-chip. The experiments were run with dilution rates (μ) between approximately 2.8 and 0.5 $h^{-1}$, which corresponds to dilution times, $t_d = \ln(2)\mu^{-1}$, between 15 and 85 min. These were achieved with dilution steps exchanging between 7 and 25% of the reactor volume with time intervals of 7 to 10 min, which alternately added fresh lysate stock or fresh buffer/DNA solution into the reactors. Dilution rates were calibrated before each experiment. DNA template concentrations used in steady-state reactions for 5n2 are: pBetI-BCD7-QacR-ssrA(LAA), 1 nM Linear; pPhlF-BCD7-SrpR-ssrA(LAA), 12 nM Linear; pQacR-BCD7-TetR-ssrA(LAA), 4 nM Linear; pSrpR-BCD7-BetI-ssrA(LAA), 24 nM Linear; pTetR-BCD7-PhlF-ssrA(LAA), 4 nM Linear; pTetR-Cerulean (ASV), 2.5 nM Plasmid, pQacR-BCD7-Citrine, 2.5 nM Plasmid. Arbitrary fluorescence values were converted to absolute concentrations from a calibration using purified Citrine, Cerulean, and mCherry.

In vivo testing for oscillators: Mother machine experiments were conducted with custom-made microfluidic chips. E. coli cells were trapped in channels of 30 μm length, 2 μm width and 1.2 μm height. Before loading onto the device, cells were grown from a frozen stock to stationery phase. Cells were then concentrated 10-fold and loaded onto the chip. Experiments were performed using LB medium supplemented with 0.075% Tween-20 at a flow rate of 400 μl/h. Oscillation traces were collected from single mother machine traps using the background subtracted average fluorescence intensity of the entire trap. The strain tested was 5n2 co-transformed with pPhlF-BCD22-sfGFP-ssrA (LAA) into JS006.

EQUIVALENTS

The present disclosure provides among other things methods and systems for rapid in vitro assembly of genetic modules. While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

The ASCII text file submitted herewith via EFS-Web, entitled "165948_010200_sequence.txt" created on Apr. 26, 2016, having a size of 2,812 bytes, is hereby incorporated by reference in its entirety.

All publications, patents and sequence database entries mentioned herein are hereby incorporated by reference in their entirety as if each individual publication or patent was specifically and individually indicated to be incorporated by reference.

REFERENCES

Chappell, J., Jensen, K., & Freemont, P. S. (2013). Validation of an entirely in vitro approach for rapid prototyping of DNA regulatory elements for synthetic biology. *Nucleic Acids Res,* 41(5), 3471-3481. doi.org/10.1093/nar/gkt052

Engler, C., Gruetzner, R., Kandzia, R., & Marillonnet, S. (2009). Golden Gate Shuffling: A One-Pot DNA Shuffling Method Based on Type IIs Restriction Enzymes. *PLoS One,* 4(5), e5553. doi.org/10.1371/journal.pone.0005553

Gibson, D. G., Young, L., Chuang, R.-Y., Venter, J. C., Hutchison, C. A., & Smith, H. O. (2009). Enzymatic assembly of DNA molecules up to several hundred kilobases. *Nat Methods,* 6(5), 343-345. doi.org/10.1038/nmeth.1318

Lee, T. S., Krupa, R. A., Zhang, F., Hajimorad, M., Holtz, W. J., Prasad, N., Lee, S. K. & Keasling J. D. BglBrick vectors and datasheets: A synthetic biology platform for gene 416 expression. *J. Biol. Eng.* 2011; 5:12

Moon, T. S., Lou, C., Tamsir, A., Stanton, B. C., & Voigt, C. A. (2012). Genetic programs constructed from layered logic gates in single cells. *Nature,* 491(7423), 249-253. doi.org/10.1038/nature11516

Niederholtmeyer, H., Sun, Z., Hori, Y., Yeung, E., Verpoorte, A., Murray, R. M., & Maerkl, S. J. (n.d.). *Rapid cell-free forward engineering of Novel Genetic Ring Oscillators.* eLife 2015; 10.7554/eLife.09771

Sarrion-Perdigones, A., Falconi, E. E., Zandalinas, S. I., Juárez, P., Fernández-del-Carmen, A., Granell, A., & Orzaez, D. (2011). GoldenBraid: An Iterative Cloning System for Standardized Assembly of Reusable Genetic Modules. *PLoS One,* 6(7), e21622. doi.org/10.1371/journal.pone.0021622

Shin, J., & Noireaux, V. (2012). An *E. coli* Cell-Free Expression Toolbox: Application to Synthetic Gene Circuits and Artificial Cells. *ACS Synth Biol,* 1(1), 29-41. doi.org/10.1021/sb200016s Sun, Z. Z., Hayes, C. A., Shin, J., Caschera, F., Murray, R. M., & Noireaux, V. (2013). Protocols for Implementing an *Escherichia coli* Based TX-TL Cell-Free Expression System for Synthetic Biology. *Journal of Visualized Experiments: JoVE,* (79), e50762-e50762. doi.org/10.3791/50762

Melissa K Takahashi, Clarmyra A. Hayes, James Chappell, Zachary Z. Sun, Richard M Murray, Vincent Noireaux, Julius B. Lucks. Characterizing and Prototyping Genetic Networks with Cell-Free Transcription-Translation Reactions. *Methods,* 15(85):60-72, 2015

Sun, Z. Z., Yeung, E., Hayes, C. A., Noireaux, V., & Murray, R. M. (2014). Linear DNA for Rapid Prototyping of Synthetic Biological Circuits in an *Escherichia coli* Based TX-TL Cell-Free System. *ACS Synth Biol,* 3(6), 387-397. doi.org/10.1021/sb400131a

---

The invention claimed is:

1. A method for in vitro assembly of genetic modules, comprising:
   (a) providing recombinant transcription units Tu1, Tu2 and TuN wherein N>=3, each recombinant transcription unit being present in a separate stage 1 vector and flanked by a first pair of restriction sites of a first type IIs enzyme, wherein the first pair of restriction sites for each recombinant transcription unit are pre-designed such that upon digestion by the first type IIs enzyme, compatible cohesive ends are generated to allow ligation of the recombinant transcription units into a linear DNA molecule having a predetermined order 5'-Tu1-TuN-Tu2-3';
   (b) providing a stage 2 vector having a second pair of restriction sites of the first type IIs enzyme, wherein the second pair of restriction sites are pre-designed such that upon digestion by the first type IIs enzyme, a first and second cohesive end are generated to allow direct ligation of the first cohesive end with Tu1 at its 5' end and direct ligation of the second cohesive end with Tu2 at its 3' end; and
   (c) assembling the recombinant transcription units and the stage 2 vector into a plasmid in a one-pot reaction comprising the first type IIs enzyme and a ligase.

2. The method of claim 1, wherein N=<9.

3. The method of claim 1, wherein the first type IIs enzyme is selected from BsaI, Eco31I, BspTN1, Bso31I, BbsI, BpuAI, BpiI, BstV21, BsmBI, Esp3I, FokI, AlwI, and BfiI.

4. The method of claim 1, further comprising constructing each recombinant transcription unit from a promoter, an untranslated region, a coding sequence and a terminator, wherein one or more of the promoter, untranslated region, coding sequence and terminator are provided from a library of modular components.

5. The method of claim 4, wherein each modular component comprises flanking restriction sites of a second type IIs enzyme.

6. The method of claim 5, wherein the second type IIs enzyme is selected from BsaI, Eco31I, BspTN1, Bso31I, BbsI, BpuAI, BpiI, BstV21, BsmBI, Esp3I, FokI, AlwI, and BfiI.

7. The method of claim 4, further comprising selecting the one or more of the promoter, untranslated region, coding sequence and terminator from the library.

8. The method of claim 1, wherein each stage 1 vector comprises a different origin of replication and/or a different selectable marker.

9. The method of claim 8, wherein the origin of replication is selected from colE1, pSC101, p15A, pBBR1, pMB1 and R6K.

10. The method of claim 8, wherein the selectable marker is selected from AmpR, KanR, CmR, ZeoR, TetR, SpecR, StrepR, NeoR, and BleR.

11. The method of claim 1, wherein the stage 2 vector further comprises a pair of restriction sites of a second type IIs enzyme that flank the second pair of restriction sites of the first type IIs enzyme.

12. The method of claim 1, further comprising cycling the recombinant transcription units between the stage 1 and stage 2 vectors to produce 2 or more copies of the recombinant transcription units.

13. The method of claim 1, further comprising providing two or more stage 2 vectors in step (b), and assembling in step (c) the recombinant transcription units and the two or more stage 2 vectors into two or more plasmids.

14. The method of claim 13, wherein each stage 2 vector comprises a different origin of replication and/or a different selectable marker.

15. The method of claim 13, further comprising assembling in step (c) up to three plasmids.

16. The method of claim 1, further comprising subjecting the plasmid to expression.

17. The method of claim 16, further comprising subjecting the plasmid to expression in an in vitro transcription-translation system.

18. The method of claim 17, further comprising amplifying the recombinant transcription units in a polymerase chain reaction prior to expression.

19. The method of claim 18, further comprising providing a first and second primer that span the first and second cohesive end, respectively, wherein the first primer partially anneals with the stage 2 vector at Tm<40° C. and partially with Tu1 at Tm<40° C., and the second primer partially anneals with the stage 2 vector at Tm<40° C. and partially with Tu2 at Tm<40° C.

20. The method of claim 16, further comprising subjecting the plasmid to in vivo expression following transformation into a host cell.

* * * * *